US012622888B2

(12) United States Patent
Jiang et al.

(10) Patent No.: US 12,622,888 B2
(45) Date of Patent: May 12, 2026

(54) PHARMACEUTICAL COMPOSITION AND APPLICATION THEREOF

(71) Applicant: SHANGHAI INSTITUTE OF MATERIA MEDICA, CHINESE ACADEMY OF SCIENCES, Shanghai (CN)

(72) Inventors: Baohong Jiang, Shanghai (CN); Linlin Wang, Shanghai (CN); Xiaoyu Wang, Shanghai (CN); Yao Fu, Shanghai (CN); Huimiao Bian, Shanghai (CN); Rongrong Xing, Shanghai (CN)

(73) Assignee: SHANGHAI INSTITUTE OF MATERIA MEDICA, CHINESE ACADEMY OF SCIENCES, Shanghai (CN)

(*) Notice: Subject to any disclaimer, the term of this patent is extended or adjusted under 35 U.S.C. 154(b) by 920 days.

(21) Appl. No.: 17/639,271

(22) PCT Filed: Aug. 28, 2020

(86) PCT No.: PCT/CN2020/112258

§ 371 (c)(1),
(2) Date: Feb. 28, 2022

(87) PCT Pub. No.: WO2021/037244

PCT Pub. Date: Mar. 4, 2021

(65) Prior Publication Data

US 2022/0331281 A1 Oct. 20, 2022

(30) Foreign Application Priority Data

Aug. 29, 2019 (CN) ........................ 201910808817.4

(51) Int. Cl.

| | |
|---|---|
| ***A61K 31/216*** | (2006.01) |
| ***A61K 9/00*** | (2006.01) |
| ***A61K 9/10*** | (2006.01) |
| ***A61K 9/19*** | (2006.01) |
| ***A61K 9/48*** | (2006.01) |
| ***A61K 36/258*** | (2006.01) |
| ***A61P 9/00*** | (2006.01) |

(52) U.S. Cl.

CPC .............. *A61K 31/216* (2013.01); *A61K 9/10* (2013.01); *A61K 9/19* (2013.01); *A61K 9/4808* (2013.01); *A61K 36/258* (2013.01); *A61P 9/00* (2018.01)

(58) Field of Classification Search

CPC ........ A61K 36/258; A61K 36/537; A61P 9/10
See application file for complete search history.

(56) References Cited

FOREIGN PATENT DOCUMENTS

| | | | | | |
|---|---|---|---|---|---|
| CN | 1579462 A | | 2/2005 | | |
| CN | 1596920 A | | 3/2005 | | |
| CN | 1726959 A | | 2/2006 | | |
| CN | 1919249 A | | 2/2007 | | |
| CN | 1919252 A | | 2/2007 | | |
| CN | 1985836 A | * | 6/2007 | | |
| CN | 101032503 A | | 9/2007 | | |
| CN | 102908355 A | * | 2/2013 | | |
| EP | 2286819 A1 | * | 2/2011 | ......... | A61K 31/7048 |

OTHER PUBLICATIONS

Patil et al. Circ Res, 2015, 116(12), 2041-2049.*
Deng et al., "Combined Salvianolic Acid B and Ginsenoside Rg1 Exerts Cardioprotection against Ischemia/Reperfusion Injury in Rats", PLoS One. Aug. 17, 2015.
Rejection decision issued in Chinese application No. 202010888436.4, dated Mar. 30, 2022, with English translation.
Notice of Reasons for Refusal issued in Japanese Application No. 2022-513868, dated Feb. 27, 2023.
International Search Report (with English translation) and Written Opinion issued in PCT/CN2020/112258, dated Nov. 27, 2020, 12 pages provided.
Deng et al., "Ginsenoside Rg1 and Rb1, in combination with salvianolic acid B, play different roles in myocardial infarction in rats", ScienceDirect, Journal of the Chinese Medical Association, vol. 78, No. 2, Nov. 2, 2015, 7 pages provided.
Office Action issued in corresponding Chinese Application No. 2020108884364, with machine translation, dated Aug. 3, 2021, 22 pages provided.
Office Action issued in corresponding Chinese Application No. 2020108884364, with machine translation, dated Dec. 28, 2021, 27 pages provided.
Kapur et al., "From bedside to bench and back again: translational studies of mechanical unloading of the left ventricle to promote recovery after acute myocardial infarction [version 1; peer review: 2 approved]", F1000Research 2018, 7(F1000 Faculty Rev):1852, 9 pages provided.

* cited by examiner

*Primary Examiner* — Kyle A Purdy
(74) *Attorney, Agent, or Firm* — HSML P.C.

(57) ABSTRACT

Provided is a pharmaceutical composition and application thereof, specifically, said pharmaceutical composition comprises: salvianolic acid B as a first active ingredient; and ginsenoside Rg1 as a second active ingredient, and the weight ratio of the first active ingredient to the second active ingredient being 5:(1-4.5). The pharmaceutical composition has a better active-ingredient proportion than the prior art, has a better therapeutic efficacy in preventing and/or treating ischemic diseases, and ischemia-reperfusion tissue or organ damage, and can be used for treating ischemia and/or ischemia-reperfusion damage of different tissues and organs.

19 Claims, 9 Drawing Sheets

Sham Ischemia reperfusion 2:5 5:2

Salvianolic acid B: ginsenoside Rg1

Sham Ischemia reperfusion 2:5 5:2

Salvianolic acid B: ginsenoside Rg1

PHARMACEUTICAL COMPOSITION AND APPLICATION THEREOF

TECHNICAL FIELD

The present invention relates to the field of medicine and specifically to a pharmaceutical composition and its application in the prevention and/or treatment of diseases such as ischemic diseases and/or ischemia-reperfusion injury.

BACKGROUND

The blood vessels are responsible for supplying blood to the tissues and organs of the whole body. If blood vessels blocked, the tissues and organs will cause diseases due to insufficient blood supply, especially the heart, brain and other tissues and organs with high demand for blood oxygen supply; with the dredging of microcirculation during shock, the relief of coronary artery spasm, and the establishment and application of the method such as arterial bypass grafting, thrombolytic therapy, percutaneous transluminal coronary angioplasty, cardiac surgery extracorporeal circulation, cardiopulmonary cerebral resuscitation, replantation of severed limbs and organs transplantation, the blood supply of many tissues and organs may restore (i.e. reperfusion) after ischemia. However, those reperfusions after ischemia sometimes not only fail to restore the function of tissues and organs, but also aggravates the dysfunction and structural damage of the tissues and organs. This phenomenon, in which tissue damage is aggravates or even irreversible after blood flow is restored on the basis of ischemia, is called ischemia-reperfusion injury.

Chinese Application No. CN2011102229806 discloses a pharmaceutical composition comprising the compound salvianolic acid B and ginsenoside Rg1, which is effective for cardiac ischemia-reperfusion injury. However, the research on the compatibility of the two is not sufficient, and it is necessary to carry out further in-depth research on the compatibility of the two components to provide pharmaceutical compositions with treatment effects on ischemia-reperfusion injury of different tissues and organs.

SUMMARY OF INVENTION

The purpose of the present invention is to provide a pharmaceutical composition for preventing and/or treating diseases such as tissue, organ ischemia, and ischemia-reperfusion injury.

The first aspect of the invention provides a pharmaceutical composition, comprising:

(a) a first active ingredient selected from the group consisting of salvianolic acid B, a stereoisomer thereof, a crystal form thereof, a pharmaceutically acceptable salt or ester thereof, an extract containing salvianolic acid B, and combinations thereof;

(b) a second active ingredient selected from the group consisting of ginsenoside Rg1, a stereoisomer thereof, a crystal form thereof, a pharmaceutically acceptable salt or ester thereof, an extract containing ginsenoside Rg1, or combinations thereof; and (c) pharmaceutically acceptable carriers;

and the weight ratio of the first active ingredient and the second active ingredient is 5:(1-4.5), wherein the weight ratio is calculated by salvianolic acid B and ginsenoside Rg1.

In another preferred embodiment, the first active ingredient comprises a purified product of salvianolic acid B or a pharmaceutically acceptable salt thereof.

In another preferred embodiment, the purity of salvianolic acid B in the purified product is ≥90%, preferably ≥95%, more preferably ≥98% or 99%, calculated by the total weight of the purified product.

In another preferred embodiment, the first active ingredient comprises salvianolic acid extract with a salvianolic acid B content C1 of ≥30wt %, wherein the content C1 is calculated by the weight of salvianolic acid.

In another preferred embodiment, the content C1 of salvianolic acid B in the extract is ≥70%, preferably ≥80%, more preferably ≥90% or ≥95%, calculated by the dry weight of the extract.

In another preferred embodiment, the second active ingredient comprises a total saponins extract with a ginsenoside Rg1 content C2 of of ≥30wt %, wherein the content C2 is calculated by the weight of the total saponins.

In another preferred embodiment, in the extract, the ginsenoside Rg1 content C2 is ≥70%, preferably ≥80%, more preferably ≥90% or ≥95%, calculated by the dry weight of the extract.

In another preferred embodiment, the weight ratio of the first active ingredient to the second active ingredient is 5:(1-4.0), preferably 5:(1.2-3.8), more preferably 5:(1.5-3.5).

In another preferred embodiment, the weight ratio of the first active ingredient to the second active ingredient is 5:(1.8-3.2), preferably 5:(1.9-3.1), more preferably 5:(2-3), most preferably 5:2.

In another preferred embodiment, the first active ingredient is salvianolic acid B and the second active ingredient is ginsenoside Rg1.

In another preferred embodiment, the dosage form of the pharmaceutical composition is selected from the group consisting of liquid dosage forms (e.g., solutions, emulsions, suspensions), solid dosage forms (e. g., lyophilized preparations), gaseous dosage forms, and semi-solid dosage forms.

In another preferred embodiment, the dosage form is selected from the group consisting of injections (e. g., an injection solutions or a powder injections), oral preparations (e. g., capsules, tablets, pills, powders, granules, syrup, oral solutions or a tinctures), sublingual preparations, preparations for respiratory, dermal, and mucosal administration, preferably, the dosage form is an injections.

The second aspect of the present invention provides a combination of active ingredients, and the combination of active ingredients comprises:

(a) a first active ingredient selected from the group consisting of salvianolic acid B, a stereoisomer thereof, a crystal form thereof, a pharmaceutically acceptable salt or ester thereof, an extract containing salvianolic acid B, and combinations thereof;

(b) a second active ingredient selected from the group consisting of ginsenoside Rg1, a stereoisomer thereof, a crystal form thereof, a pharmaceutically acceptable salt or ester thereof, an extract containing ginsenoside Rg1, or any combinations thereof;

and the weight ratio of the first active ingredient and the second active ingredient is 5:(1-4.5), wherein the weight ratio is calculated by salvianolic acid B and ginsenoside Rg1.

In another preferred embodiment, the combination of active ingredients consists of (a) the first active ingredient and (b) the second active ingredient.

The third aspect of the present invention provides a pharmaceutical kit, the kit comprises:

a first pharmaceutical composition, comprising: (a) a first active ingredient selected from the group consisting of salvianolic acid B, a stereoisomer thereof, a crystalline form thereof, a pharmaceutically acceptable salt or ester thereof, an extract containing salvianolic acid B, or a combination thereof; and a pharmaceutically acceptable carrier;

a second pharmaceutical composition, comprising: (b) a second active ingredient selected from the group consisting of ginsenoside Rg1, a stereoisomer thereof, a crystal form thereof, a pharmaceutically acceptable salt or ester thereof, an extract containing ginsenoside Rg1, or combinations thereof; and a pharmaceutically acceptable carrier;

wherein, the first pharmaceutical composition and the second pharmaceutical composition are administered in combination, wherein the weight ratio of the first active ingredient to the second active ingredient is 5:(1-4.5), wherein the weight ratio is calculated by salvianolic acid B and ginsenoside Rg1.

In another preferred embodiment, the first pharmaceutical composition and the second pharmaceutical composition are different (or independent) pharmaceutical composition or the same pharmaceutical composition.

The fourth aspect of the present invention provides the use of the pharmaceutical composition according to the first aspect of the present invention, the combination of the active ingredients according to the second aspect of the present invention, or the pharmaceutical kit according to the third aspect of the present invention for preparing a medicament or pharmaceutical kit for (i) preventing and/or treating an ischemic disease; (ii) preventing and/or treating ischemia-reperfusion injury; or (iii) inhibiting lactate dehydrogenase.

In another preferred embodiment, the medicament or kit is used for (I) prevention and/or treatment of ischemic heart disease; (ii) prevention and/or treatment of ischemia-reperfusion injury; (iii) inhibition of lactate dehydrogenase and/or (iv) prevention and/or treatment of ischemic disease.

In another preferred embodiment, the ischemic disease is selected from the group consisting of tissue and organ damage caused by acute ischemia and/or tissue and organ damage caused by chronic ischemia.

In another preferred embodiment, the ischemic disease is selected from the group consisting of tissue and organ ischemic injury due to primary lesions of tissues and blood vessels, and/or ischemic lesions due to secondary causes, such as trauma-induced vascular disconnection, inflammation-induced vascular occlusion, tumor-induced vascular compression.

In another preferred embodiment, the ischemic disease is selected from the group consisting of ischemic heart disease, ischemic stroke (e. g., acute cerebral infarction), ischemic liver injury, pulmonary embolism, ischemic kidney injury, ischemic nerve injury, and combinations thereof.

In another preferred embodiment, the ischemic heart disease comprises coronary heart disease, myocardial infarction, angina, myocardial fibrosis, heart failure, or any combination thereof.

In another preferred embodiment, the ischemia-reperfusion injury is tissue or organ injury caused by reperfusion.

In another preferred embodiment, the tissue or organ is selected from the group consisting of heart, brain, liver, spleen, lung, kidney, muscle, nerve, and combinations thereof. In another preferred embodiment, the tissue or organ is selected from the group consisting of liver, spleen, lung, kidney, brain, nerve, and combinations thereof.

In another preferred embodiment, the tissue or organ is selected from the group consisting of heart, brain, and combination thereof.

In another preferred embodiment, the medicament or kit is also used for improving myocardial hypertrophy induced by pulmonary embolism. In another preferred embodiment, the medicament or kit is also used for improving the diastolic function of the heart with reperfusion injury; preferably, the diastolic function of the heart includes the diastolic rate of the heart.

In another preferred embodiment, the medicament or kit is also used for improving the contractile function of the heart (e. g., the rate of contraction of the heart).

In another preferred embodiment, the medicament or kit is used for improving the reperfusion injury of the kidney, preferably including improving the structure of kidney.

In another preferred embodiment, the tissue or organ injury is post-surgery reperfusion injury, and preferably, the surgery is selected from the group comsisting of arterial bypass surgery, thrombectomy or thrombolytic therapy, percutaneous transluminal coronary angioplasty, cardiac surgery under extracorporeal circulation, cardiac arrest, lung and/or cerebral resuscitation, limb replantation or organ transplantation, or other major surgical reperfusion injury.

It should be understood that within the scope of the present invention, the above-described technical features of the present invention and the technical features described in detail below (e.g., embodiments) may be combined with each other to constitute a new or preferred technical solution. Limited by space, it will not be repeated here.

DETAILED DESCRIPTION OF THE INVENTION

Figure 1:
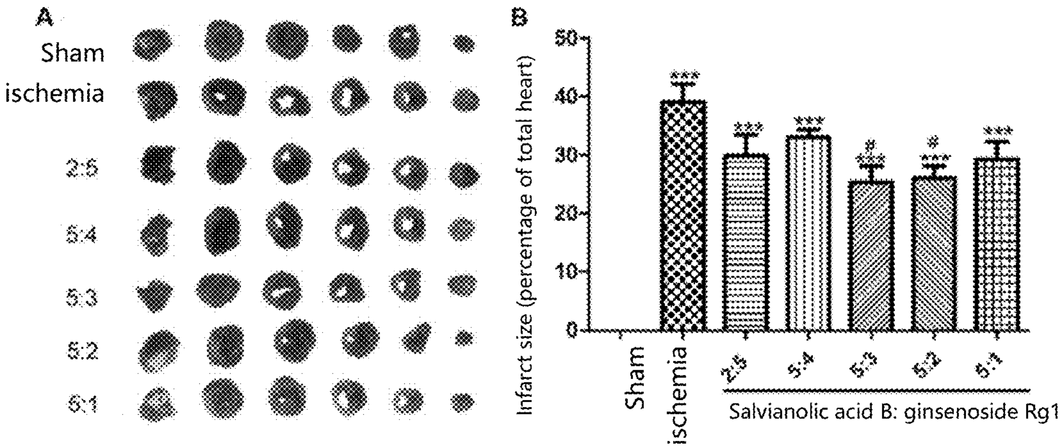
FIG. 1 shows the effect of salvianolic acid B/ginsenoside Rg1 on reducing the infarct size of the heart on an animal model of myocardial infarction. (A) representative photographs of TTC staining of heart sections; (B) quantification of infarct size (percentage of area of infarcted area over the whole heart).

After extensive and in-depth research, through a large number of screening and testing, the inventors provided a pharmaceutical composition containing salvianolic acid B and ginsenoside Rg1 as the active ingredients. Compared with the prior art, the pharmaceutical composition of the present invention has a more excellent therapeutic effect on ischemic diseases and ischemia-reperfusion injury of tissues or organs; and surprisingly, the composition of the present invention not only have therapeutic effects on ischemia-reperfusion injury of heart, brain and liver, but also of kidney and other organs, and can be used for ischemia-reperfusion injury of various tissues and organs. On this basis, the present invention was completed.

Terms

Unless otherwise defined, all technical and scientific terms used herein have the same meaning as commonly understood by those skilled in the art.

As used herein, the terms "include," "comprise" and "contain," are used interchangeably to include not only closed definitions, but also semi-closed, and open definitions. In other words, the term includes "consist of" and "substantially consist of".

As used herein, the term "stereoisomer" is intended to include all isomeric forms (e. g., enantiomeric, diastereomeric, and geometric (or conformational isomers): for example, R, S configurations of those with asymmetric centers, (Z), (E) isomers of those containing double bonds, etc. Thus, a single stereochemical isomer of the active ingredient of the present invention or a mixture of enantiomers, diastereomers or geometric isomers (or conformational isomers) thereof are within the scope of the present invention.

The active ingredients of the invention may be amorphous, crystalline or mixtures thereof.

As used herein, "pharmaceutically acceptable salt" refers to a salt suitable for use as a medicament formed by active ingredient compounds of the present invention and an acid or base. Pharmaceutically acceptable salts include inorganic and organic salts. A class of preferred salts is salts formed by the compounds of active ingredients of the present invention and an acid. Acids suitable for forming the salt include (but are not limited to): inorganic acids such as hydrochloric acid, hydrobromic acid, hydrofluoric acid, sulfuric acid, nitric acid, phosphoric acid, etc., organic acid such as formic acid, acetic acid, propionic acid, oxalic acid, malonic acid, succinic acid, fumaric acid, maleic acid, lactic acid, malic acid, tartaric acid, citric acid, picric acid, methanesulfonic acid, toluenesulfonic acid, benzenesulfonic acid, etc.; and acidic amino acids such as aspartic acid and glutamic acid, etc. A class of preferred salt is the salt formed by the compounds of active ingredient of the present invention and a base. Bases suitable for forming the salt include (but are not limited to): inorganic bases such as sodium hydroxide, potassium hydroxide, sodium carbonate, sodium bicarbonate, sodium phosphate, etc., organic bases such as ammonia, triethylamine, diethylamine, etc.

As used herein, "pharmaceutically acceptable ester" refers to an ester suitable for use as a drug formed by a active ingredient compound of the present invention and an acid or alcohol. A class of preferred ester is esters formed by one or more hydroxyl groups of the active ingredient of the present invention and acids, and an acid suitable for forming the ester include, but are not limited to: phosphoric acid, formic acid, acetic acid, propionic acid, oxalic acid, malonic acid, succinic acid, fumaric acid, maleic acid, lactic acid, malic acid, tartaric acid, citric acid, picric acid, methanesulfonic acid, benzanesulfonic acid, benzenesulfonic acid, etc.; another class of preferred esters are esters formed by the carboxyl group of the active ingredient of the present invention with alcohols, suitable alcohols for forming esters include, but are not limited to: C1-C6 alkyl-OH, such as methanol, ethanol, n-propanol, isopropanol, etc.

Unless otherwise specified, in the pharmaceutical composition, the weight ratio is calculated based on the original compound of salvianolic acid B and ginsenoside Rg1.

The "prevention" and "treatment" described in the present invention include delaying and terminating the progression of the disease, or eliminating the disease, and 100% suppression, elimination and reversion are not required. In some embodiments, compared with the levels observed in the absence of the compositions or pharmaceutical compositions of the present invention, the compositions or pharmaceutical compositions of the present invention prevent, reduce, inhibit, and/or reverse, ischemia-reperfusion injury, for example, by at least about 10%, at least about 30%, at least about 50%, or at least about 80%.

As used in the present invention, the term "SalB" and "salvianolic acid B" can be used interchangeably; the term "Rg1" and "ginsenoside Rg1" can be used interchangeably.

First Active Ingredient

In the present invention, the first active ingredient is selected from the group consisting of salvianolic acid B, a stereoisomer thereof, a crystal form thereof, a pharmaceutically acceptable salt or an ester thereof, an extract containing salvianolic acid B, and combinations thereof.

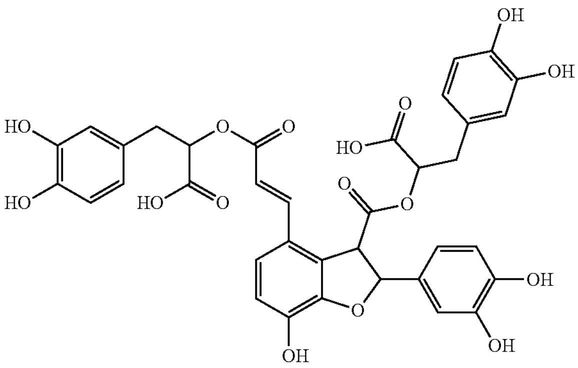

Salvianolic acid B

In another preferred embodiment, the first active ingredient comprises a purified product of salvianolic acid B or a pharmaceutically acceptable salt thereof.

In another preferred embodiment, the purity of salvianolic acid B in the purified product is ≥90%, preferably ≥95%, more preferably ≥98% or 99%, calculated by the total weight of the purified product.

In another preferred embodiment, the first active ingredient comprises salvianolic acid extract with a salvianolic acid B content C1 of ≥30wt %, wherein the content C1 is calculated by the weight of salvianolic acid.

In another preferred embodiment, the content C1 of salvianolic acid B in the extract is ≥70%, preferably ≥80%, more preferably ≥90% or ≥95%, calculated by the dry weight of the extract.

Second Active Ingredient

In the present invention, the second active ingredient selected from the group consisting of ginsenoside Rg1, a stereoisomer thereof, a crystal form thereof, a pharmaceutically acceptable salt or ester thereof, an extract containing ginsenoside Rg1, and combinations thereof.

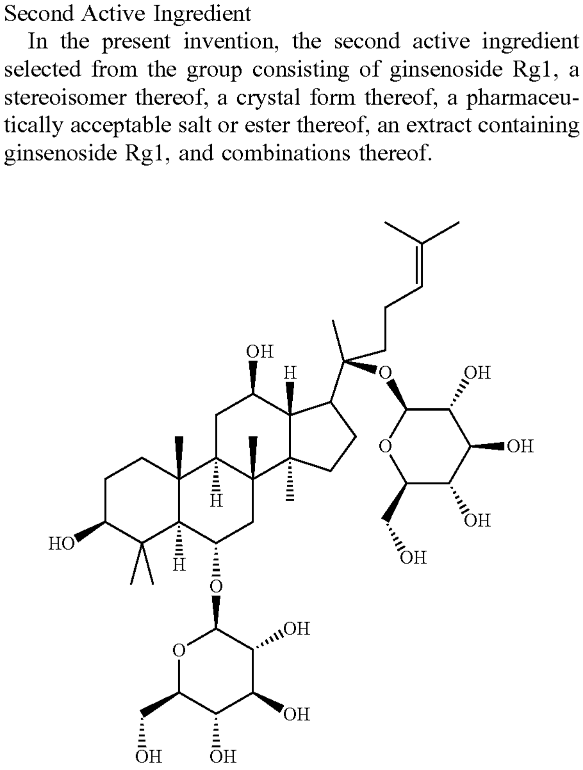

Ginsenoside Rg1

In another preferred embodiment, the second active ingredient comprises a total saponin extract with a ginsenoside Rg1 content C2 of ≥30wt %, wherein the content C2 is calculated by the weight of the total saponin.

In another preferred embodiment, in the extract, the content C2 of ginsenoside Rg1 is ≥70%, preferably ≥80%, more preferably ≥90% or ≥95%, calculated by the dry weight of the extract.

Pharmaceutical Compositions, Active Ingredients Combination, Kits

The invention provides a pharmaceutical composition, including:

(a) a first active ingredient selected from the group consisting of salvianolic acid B, a stereoisomer thereof, a crystal form thereof, a pharmaceutically acceptable salt or ester thereof, an extract containing salvianolic acid B, and combinations thereof;

(b) a second active ingredient selected from the group consisting of ginsenoside Rg1, a stereoisomer thereof, a crystal form thereof, a pharmaceutically acceptable salt or ester thereof, an extract containing ginsenoside Rg1, or combinations thereof; and (c) pharmaceutically acceptable carriers;

and the weight ratio of the first active ingredient and the second active ingredient is 5:(1-4.5), wherein the weight ratio is calculated by salvianolic acid B and ginsenoside Rg1.

In another preferred embodiment, the weight ratio of the first active ingredient to the second active ingredient is 5:(1-4.0), preferably 5:(1.2-3.8), more preferably 5:(1.5-3.5).

In another preferred embodiment, the weight ratio of the first active ingredient to the second active ingredient is 5:(1.8-3.2), preferably 5:(1.9-3.1), more preferably 5:(2-3), most preferably 5:2.

In another preferred embodiment, the first active ingredient is salvianolic acid B and the second active ingredient is ginsenoside Rg1.

The dosage form of the pharmaceutical composition is selected from the group consisting of liquid preparations (e. g., solutions, emulsions, suspensions), and solid preparations (e. g., lyophilized preparations).

In another preferred embodiment, the dosage form is selected from the group consisting of injections (such as injection liquids or powder injections), and oral preparations (such as capsules, tablets, pills, powders, granules, syrups, oral liquids or tinctures), and more preferably, the dosage form is injections.

In the pharmaceutical composition of the present invention, the first active ingredient and the second active ingredient may be separately prepared into preparations or mixed together to be prepared into a preparation.

The pharmaceutical composition of the present invention comprises a first active ingredient and/or a second active ingredient in a safe and effective amount. Among them, "safe and effective amount" refers to an amount of active ingredients that is sufficient to significantly improve the condition without causing serious side effects. Typically, the pharmaceutical composition contains 1-2000 mg of the active ingredients of the present invention per dose, and more preferably 10-500 mg of the active ingredient of the present invention per dose. Preferably, the "dose" is a capsule, a tablet, or an injection, etc.

In the present invention, "pharmaceutically acceptable carrier" refers to one or more compatible solid or liquid filler or gel substances that are suitable for human use and must have sufficient purity and sufficiently low toxicity. "Compatibility" herein means that the components of the composition are capable of admixing with the first active ingredient and/or the second active ingredient without significantly reducing the efficacy of the first active ingredient and/or the second active ingredient. Part of examples of pharmaceutically acceptable carriers are cellulose and its derivatives (such as sodium carboxymethyl cellulose, sodium ethyl cellulose, cellulose acetate, etc.), gelatin, talc, solid lubricants (such as stearic acid and magnesium stearate), calcium sulfate, vegetable oils (such as soybean oil, sesame oil, peanut oil, olive oil, etc.), polyols (such as propylene glycol, glycerin, mannitol, sorbitol, etc.), emulsifiers (such as Tween®), wetting agents (such as sodium dodecyl sulfate), colorants, flavoring agents, stabilizers, antioxidants, preservatives, pyrogen-free water, and the like.

The invention also provides a combination of active ingredients, the combination of active ingredients comprises:

(a) a first active ingredient selected from the group consisting of salvianolic acid B, a stereoisomer thereof, a crystal form thereof, a pharmaceutically acceptable salt or ester thereof, an extract containing salvianolic acid B, and combinations thereof;

(b) a second active ingredient selected from the group consisting of ginsenoside Rg1, a stereoisomer thereof, a crystal form thereof, a pharmaceutically acceptable salt or ester thereof, an extract containing ginsenoside Rg1, or combinations thereof;

and the weight ratio of the first active ingredient and the second active ingredient is 5:(1-4.5), wherein the weight ratio is calculated by salvianolic acid B and ginsenoside Rg1.

In another preferred embodiment, the combination of active ingredients consists of (a) the first active ingredient and (b) the second active ingredient.

In the combination of active ingredients, the first active ingredient and the second active ingredient may be independent between each other or may be combined together existing in the form of active ingredients composition.

The invention also provides a kit, the kit comprises:

a first pharmaceutical composition, comprising: (a) a first active ingredient selected from the group consisting of salvianolic acid B, a stereoisomer thereof, a crystalline form thereof, a pharmaceutically acceptable salt or ester thereof, an extract containing salvianolic acid B, or a combination thereof; and a pharmaceutically acceptable carrier;

a second pharmaceutical composition, comprising: (b) a second active ingredient selected from the group consisting of ginsenoside Rg1, a stereoisomer thereof, a crystal form thereof, a pharmaceutically acceptable salt or ester thereof, an extract containing ginsenoside Rg1, or combinations thereof; and a pharmaceutically acceptable carrier;

and, the first pharmaceutical composition and the second pharmaceutical composition are administered in combination, wherein the weight ratio of the first active ingredient to the second active ingredient is 5:(1-4.5), wherein the weight ratio is based on salvianolic acid B and ginsenoside Rg1.

In another preferred embodiment, the kit further includes a instruction.

In another preferred embodiment, the first pharmaceutical composition and the second pharmaceutical composition are different (or independent) pharmaceutical compounds or the same pharmaceutical composition.

In another preferred embodiment, the first pharmaceutical composition and the second pharmaceutical composition are administered simultaneously, separately or sequentially.

The pharmaceutical composition, the combination of active ingredients and the kit of the invention can be prepared with conventional methods and equipment.

Use and Method of Application

The invention provides a use of the pharmaceutical composition, the combination of active ingredients, or the kit described herein for the preparation of a medicament or kit used for (i) prevention and/or treatment of ischemic diseases; (ii) prevention and/or treatment of ischemia-reperfusion injury; and/or (iii) inhibition of lactate dehydrogenase.

In the present invention, the ischemic disease refers to injury or lesion of tissue or organ due to ischemia. The term "ischemia" refers to a decrease in the blood supply to a tissue or organ from a normal value, and in particular to the inability of the blood supplied to the tissue or organ to meet the metabolic needs of the tissue or organ.

The active ingredient of the invention has obvious therapeutic effect on ischemic diseases. Common ischemic diseases include but are not limited to ischemic heart disease, ischemic stroke, ischemic liver injury, ischemic lung injury, ischemic kidney injury, or any combination thereof.

In the present invention, the ischemic heart disease is a heart disease caused by myocardial ischemia and hypoxia due to changes in coronary circulation. Common ischemic heart diseases include the following groups (but not limited to): coronary heart disease, myocardial infarction, myocardial fibrosis, angina pectoris, or any combination thereof.

In the present invention, the ischemia-reperfusion injury includes tissue or organ injury caused by reperfusion. The tissues or organs including (but are not limited to): heart, liver, spleen, lung, kidney, brain, muscle, nerve, or any combination thereof. The tissue or organ injury also includes post-surgery reperfusion injury including, but not limited to, arterial bypass surgery, thrombolytic therapy, percutaneous transluminal coronary angioplasty, cardiopulmonary bypass cardiac surgery, cardiac, pulmonary and/or cerebral resuscitation after cardiac arrest, limb replantation, or organ transplantation. The reperfusion injury also includes reperfusion injury after microcirculation dredging after shock, and reperfusion injury after relief of coronary artery spasm.

In the present invention, the prevention and/or treatment of ischemic diseases, prevention and/or treatment of ischemia-reperfusion injury and other applications, including preventive applications, as well as post-event improvement applications. For example, for reperfusion injury, including the administration of the pharmaceutical composition, active ingredient composition or kit of the present invention before, during, and/or after reperfusion to protect, repair the tissues or organs after reperfusion injury, or improve or enhance the function thereof.

In the pharmaceutical composition, the combination of active ingredients or the kit of the present invention, the first active ingredient and the second active ingredient may also be administered in combination with other pharmaceutically acceptable compounds, including (but not limited to): antihypertensive drugs, hypolipidemic drugs, hypoglycemic drugs, antiplatelet aggregation drugs, etc.

The pharmaceutical composition, combination of active ingredients or kit of the present invention can also be used to inhibit lactate dehydrogenase. Lactate dehydrogenase (LDH) is an enzyme required to convert sugar into cellular energy, which exists in various organs and tissues of the body, such as liver, heart, pancreas, kidney, skeletal muscle, lymphoid tissue and blood cells. Lactate dehydrogenase is involved in the final step of glycolysis in which pyruvate is converted into lactic acid. Although normal tissues usually use glycolysis only when the oxygen supply is insufficient, cancer tissues rely heavily on aerobic glycolysis and are irrelevant to the oxygen supply level. LDH inhibitors are used for pathology involving metabolic transformation from oxidative phosphorylation to glycolysis, for example, they can be used to (but not limited to): treat patients with cancer, fibrosis, or other conditions in which metabolic transformation from oxidative phosphorylation to glycolysis occurs. At the same time, lactate dehydrogenase is an enzyme responsible for converting glyoxylic acid into oxalic acid in the mitochondrial/peroxisomal glycine metabolic pathway of liver and pancreas. Inhibition of LDH can be used to treat chronic kidney disease, such as hyperoxaluria. The pharmaceutical composition of the present invention can reduce the concentration of LDH in blood and/or inhibit the activity of LDH, and can be used as an LDH inhibitor.

In the pharmaceutical composition, combination of active ingredients or kit of the present invention, the first active ingredient and the second active ingredient can be administered simultaneously, separately or sequentially.

In the pharmaceutical composition, combination of active ingredients or kit of the present invention, the mode of administration of the first active ingredient and the second active ingredient is not particularly limited, and representative modes of administration include, but are not limited to, oral, rectal, parenteral (intravenous, intramuscular or subcutaneous), and topical administration.

Solid dosage forms for oral administration include capsules, tablets, pills, powders and granules. In these solid dosage forms, the active ingredients are mixed with at least one conventional inert excipient (or carrier), such as sodium citrate or dicalcium phosphate, or mixed with: (a) fillers or compatibilizers, such as starch, lactose, sucrose, glucose, mannitol and silicic acid; (b) binders, e.g., hydroxymethylcellulose, alginate, gelatin, polyvinylpyrrolidone, sucrose, and gum arabic; (c) humectants, e.g., glycerol; (d) disintegrants, e.g., agar, calcium carbonate, potato starch or tapioca starch, alginic acid, certain complex silicates, and sodium carbonate; (e) slow solvents, e.g., paraffin; (f) absorption accelerators, e.g., quaternary amine compounds; (g) wetting agents, e.g., cetearyl alcohol and glycerol monostearate; (h) sorbents, e.g., kaolin; and (i) lubricants, e.g., talc, calcium stearate, magnesium stearate, solid polyethylene glycol, sodium dodecyl sulfate, or mixtures thereof. In capsules, tablets and pills, the dosage forms may also contain buffers.

Solid dosage forms such as tablets, sugar pills, capsules and granules may be prepared using coating and shell materials such as casing and other materials well known in the art. They may comprise an opacifying agent, and the release of the active ingredient in such a composition may be released in a delayed manner in a part of the digestive tract. Examples of embedding components that can be employed are polymeric substances and wax substances. If necessary, the active ingredient may also form a microcapsule form with one or more of the excipients described above.

Liquid dosage forms for oral administration include pharmaceutically acceptable emulsions, solutions, suspensions, syrups or tinctures. In addition to the active ingredients, the liquid dosage form may contain inert diluents conventionally used in the art, such as water or other solvents, solubilizers and emulsifiers, for example, ethanol, isopropanol, ethyl carbonate, ethyl acetate, propylene glycol, 1,3-butanediol, dimethylformamide and oils, especially cottonseed oil, peanut oil, corn germ oil, olive oil, castor oil and sesame oil, or mixtures thereof.

In addition to these inert diluents, the composition may also contain auxiliaries such as wetting agents, emulsifiers, suspending agents, sweeteners, flavoring agents and flavors.

In addition to the active ingredient, the suspension may comprise suspending agents, such as ethoxylated isooctadecanol, polyoxyethylene sorbitol and dehydrated sorbitol esters, microcrystalline cellulose, methanolic aluminum, agar, and any mixtures thereof.

The composition for parenteral injection may comprise physiologically acceptable sterile aqueous or anhydrous solutions, dispersions, suspensions or emulsions, and sterile powders for redissolution into sterile injectable solutions or dispersions. Suitable aqueous and non-aqueous carriers, diluents, solvents, or excipients include water, ethanol, polyols, and suitable mixtures thereof.

The dosage forms for topical administration of the active ingredients of the present invention include ointments, powder, patches, propellants and inhalants. The active ingredient is mixed under sterile conditions with a physiologically acceptable carrier and any preservatives buffers or propellants as may be required.

In the pharmaceutical composition, the combination of active ingredients or the kit of the present invention, based on the total amount of salvianolic acid B and ginsenoside Rg1, the general range of the therapeutic effective dose of the active ingredients will be: about 1-2000 mg/day, about 10-about 1000 mg/day, about 10-about 500 mg/day, about 10-about 250 mg/day, about 10-about 100 mg/day, or about 10-about 80 mg/day. The therapeutically effective dose will be given in one or more units. However, it should be understood that a particular dose of the active ingredient of the invention for any particular patient will depend on a number of factors, such as, for example, age, sex, weight, general health, diet, individual response of the patient to be treated, time of administration, severity of the disease to be treated, dosage form, mode of application, and concomitant medication. The therapeutic effective dose of a given situation can be determined by routine experiments and is within the scope of clinician or physician's ability and judgment. In any case, the active ingredient will be administered in multiple doses based on the individual condition of the patient and in a manner that allows delivery of a therapeutically effective amount.

The main advantages of the invention include:

1. Compared with the prior art, the pharmaceutical composition of the present invention has a better active ingredients ratio, and has a better therapeutic effect on the treatment of ischemic diseases and ischemia-reperfusion injury (such as excellent effect of reducing infarct size and improving function of tissues and organs).
2. The pharmaceutical composition of the present invention has therapeutic effect on reperfusion injury of not only heart, but also different organs such as brain, liver, lung and kidney, and can be widely applied to ischemia-reperfusion injury of various tissues and organs
3. The pharmaceutical composition of the present invention also has the effect of inhibiting lactate dehydrogenase, can quickly reduce the content and/or activity of lactate dehydrogenase in blood, and can be used as a lactate dehydrogenase inhibitor for diseases related to lactate dehydrogenase.

The present invention will be further explained below in conjunction with specific embodiments. It should be understood that these embodiments are only used to illustrate the present invention and not to limit the scope of the present invention. In the following examples, the test methods without specific conditions are usually in accordance with conventional conditions or the conditions recommended by the manufacturer. Unless otherwise specified, percentages and parts are percentages by weight and parts by weight.

1. Reagents and Materials

1.1 Animals 134 clean male Wistar rats weighing 220±10 g; wherein 56 rats were used for the study of the protective effect of combined drugs with different ratios on the heart of myocardial infarction rats; 16 rats were used for the study of the protective effect of combined drugs on ischemia-reperfusion heart; 32 rats were used for the study of the protective effect of combined drugs on ischemia-reperfusion kidney; 30 rats were used to evaluate the preventive effect of combined drugs on pulmonary embolism and its complications.

96 clean male SD rats weighing 220±10 g; wherein 30 rats were used for the study of the protective effect of combined drugs on ischemic cerebral infarction; 50 rats were used for the study of the protective effect of combined drugs on cerebral ischemia-reperfusion injury; 16 rats were used for the study of the protective effect of combined drugs on ischemia-reperfusion liver.

Wistar and SD rats are provided by the Shanghai Experimental Animal Center of the Chinese Academy of Sciences, and are raised in the SPF animal room of the Experimental Animal Center of the Shanghai Institute of Materia Medica, Chinese Academy of Sciences, with a constant temperature of 22±2° C., 12 h light, standard diet, and free for drinking water.

Mode of administration: if not specified, the mode of administration in the examples are tail vein injection.

1.2 Main Reagents and Consumables

| ReagentsName | Source |
|---|---|
| Salvianolic acid B (purity ≥99%) | Shanghai Yousi Biotechnology Co., Ltd. |
| Ginsenoside Rg1 (purity ≥99%) | Shanghai Yousi Biotechnology Co., Ltd. |
| pentobarbital sodium | Shanghai Sinopharm Group Chemical Reagents Co., Ltd. |
| hematoxylin staining solution | Shanghai Yifan Biotechnology Co., Ltd. |
| Eosin staining solution | Shanghai Yifan Biotechnology Co., Ltd. |
| Neutral gum | Shanghai Sinopharm Group Chemical Reagent Co., Ltd. |
| Periodic Schiff staining solution | Nanjing Jiancheng Technology Co., Ltd. |

1.3 Main Instruments

| Name of instrument | Model | Source |
|---|---|---|
| Animal ventilator | ALT-V9 | Shanghai Alcott Biotechnology Co., Ltd. |
| Eight-channel physiological recorder | AD Powerlab 8/30 | AD Instruments, Australia |
| Ultra low temperature refrigerator | DW-86L626 | Qingdao Haier Biomedical Co., Ltd. |
| Automatic dehydrator | EICA TP 1020 | German Leica Company |
| Embedding machine | EG1150 H | German Leica Company |
| Section cutter | Leica RM 2016 | German Leica Company |
| Floatation bath | HI1210 | German Leica Company |
| Cooling stage | Leica EG 150C | German Leica Company |
| Slide Drier | HI1220 | German Leica Company |
| Stereo microscope | SZX7 | Japan Olympus company |
| Orthographic fluorescence microscope | BX51 | Japan Olympus company |

1.4 General Experimental Method

Separation and Treatment of Blood

Pentobarbital sodium (40 mg/kg) was injected intraperitoneally to anesthetize rats and fixed on the mouse plate. The abdomen was cut open along the median line with scissors, the contents in abdominal cavity were taken out, the liquid in the abdominal cavity was wiped with a dry cotton ball, and the blood was taken from the abdominal aorta and into a 2 ml EP tube with a 5 mL syringe, then the blood was placed on ice for 0.5 hours, centrifuged for 10 min at 4° C. with 8000 r/min, the supernatant was taken and the serum is divided into 0.5 ml EP tubes, store in −80° C. refrigerator for later use.

TTC Staining 0.5 g TTC powder was dissolved in 100 ml PBS and stored in the dark. It is currently prepared for currently use. The fresh tissue was cut into multiple pieces, placed in a small box with a lid, added TTC solution and then placed in a wet box with protection from light, incubated in a constant temperature oven at 37° C. for 20 min, during this period, the tissues were turned over several times to contact the dye solution evenly, then taken out for photographing after 20 min.

Fixation, Dehydration, Paraffin Embedding, and Sectioning of Samples 100 ml of formaldehyde, 4 g of sodium dihydrogen phosphate and 6.5 g of disodium hydrogen phosphate are dissolved in 900 mL of distilled water to prepare paraformaldehyde fix solution with a volume ratio of 10%. After being fixed in paraformaldehyde fix solution for 72 h, the tissue was washed with water for 2 h, then placed in a dehydrator with a predefined program for automatic dehydration, treated with 75% ethanol for 1.5 h, 95% ethanol for 1.5 h, 100% ethanol for 1.5 h, xylene for 1.5 h and paraffin for 1.5 h in turn. Open the paraffin embedding machine 2 h in advance to melt paraffin, and control the temperature at 60° C. After the paraffin was melted, the dehydrated tissues are embedded with paraffin, poured into the embedding box, the paraffin-soaked tissue block was placed into a embedding frame with heated tweezers, gently moved to a cooling stage, then the paraffin block was removed after the paraffin is solidified to prepare for sectioning. Before section, the paraffin block was placed into the refrigerator for precooling, then cut into paraffin sections with a thickness of 5 μm continuously by a section cutter. The sections were unfolded on the 38° C. warm water in spreading machine, fished out with polylysine coated glass slides, and air-dried for subsequent histopathological staining.

HE Staining

The tissue sections were placed on a 65° C. slide drier for 60 min, putted into xylene quickly to dewax for 15 min, then soaked in 100%, 95% and 75% ethanol for 5 min in turn, rinsed with flowing water for 5 min, placed in hematoxylin dye solution for 15 min, washed with water for 5 min, and then add 1% ethanol hydrochloride differentiation solution (preparation: 3 mL concentrated hydrochloric acid was added into 300 mL 75% ethanol and stirred evenly) for 3 s, returned to blue with flowing water for 5 min, putted into 1% eosin solution for 10 min, the excess eosin dye solution was quickly rinsed off, and then transferred to 75% ethanol for 4 min, 95% ethanol for 4 min, 100% ethanol for 5 min, and clear xylene for 15 min, finally seal the sections with xylene neutral gum, after the gum is air-dried, general pictures were taken with a stereomicroscope, and local magnification pictures were taken with a BX51 microscope.

PAS Staining

The tissue sections were placed on a 65° C. slide drier for 60 min, putted into xylene quickly to dewax for 15 min, soaked in 95%, 70% and 30% ethanol for 2 min in turn, and soaked in distilled water for 2 minutes, a prepared reagent I application dye solution was added dropwise to the sample on the glass slide to cover the samples completely, the glass slide was gently laid on the dyeing rack, and incubate at room temperature for 8-15 minutes in the dark. The stained slide was taken out and rinsed slowly with flowing water for 3-5 minutes. Before the slide is completely dried, a reagent II application solution was added dropwise to the sample on the glass slide sample, blowing the dye solution with ear washing balls to cover the sample completely, and then incubating at room temperature for 8-15 minutes. After the incubation, the stained slide was taken out and rinsed slowly with flowing water for 30-60 s, and air-dried. A reagent III counter stain was added dropwise for 20-30 seconds, then rinsed with flowing water, sealed with mounting medium after drying, and after the mounting medium was air-dried, general picture were taken with a stereomicroscope, and local magnification pictures were taken with a BX51 microscope.

Biochemical Index Detection

LDH was detected according to lactate dehydrogenase assay kit (lactic acid substrate method, Xisenmeikon Biotechnology (Wuxi) Co., Ltd., batch number: R8004), and rat serum was detected by automatic biochemical analyzer (JCA-BM6010/C, Xisenmeikon Medical Electronics (Shanghai) Co., Ltd.).

Hemodynamic Testing

After 40 mg/kg pentobarbital sodium was injected intraperitoneally to anesthetize the rats, the right common carotid artery was separated and inserted into Miller catheter, a Powerlab8/30 physiological recorder (ML870, ADINSTRUMENTS) was used to record carotid artery pressure, left ventricular maximum systolic rate, left ventricular maximum diastolic rate, left ventricular end diastolic pressure and other hemodynamic indexes.

Calculation of Index of Left Lung and Right Lung

Rats were weighed and anesthetized by intraperitoneal injection of 30 mg/kg Choutet, then the left lung and right lung were separated and weighed. The left lung indexes and right lung indexes were calculated based on the ratio of weight of left lung or right lung to body weight, respectively.

Quantification of Interstitial Lung Area

Quantitative analysis of hematoxylin-eosin stained lung tissue. The lung parenchyma such as trachea, bronchus and alveoli of each sample were removed, the remaining purple part represents the lung interstitium, each tissue samples was photographed at the same magnification to quantify the lung interstitium area.

Immunohistochemical Staining to Investigate the Infiltration of Neutrophils

The paraffin-embedded tissue was dried at 65° C. for 45-50 minutes; then treated with xylene for 15 minutes, absolute ethanol for 5 minutes, 95% ethanol for 5 minutes, 75% ethanol for 3 minutes, flowing water for 1 minute, and dewaxing to an aqueous phase; under microwave conditions, the antigen was repaired with citric acid repair solution; incubated with 10% goat serum for 30 minutes at 37° C.; incubated with CD44 antibody overnight at 4° C.; incubated with secondary antibody for 1 hour at 37° C.; DAB solution was added dropwise for 40 s; then redye with hematoxylin for 15 minutes; differentiated with 1% ethanol hydrochloride for 5 seconds; cleared with xylene; and then sealed with neutral gum. Image Pro Plus software was used to quantify the positive cell area and optical density of each sample, and the average optical density value was calculated by the ratio of optical density to positive cell area.

Behavioral Testing of Animals

Longa score, NSS score and EBST test were performed on all experimental animals two days before operation and one day after operation.

A. Longa score: 0: normal, no neurological damage; 1: left front paw cannot be fully extended, mild neurological damage; 2: when walking, the rat turns to the left side (hemiplegic side), moderate neurological damage; 3: when walking, the rat body dumps to the left side (hemiplegic side), severe neurological damage; 4: the rat cannot walk spontaneously, with loss of consciousness.

B. NSS scoring method: 0: normal neurological function; 1: mild neurological deficit (left forelimb flexion during tail lifting); 2: moderate neurological deficit (turning to the left when walking); 3: moderate neurological deficit (tilt to the left); 4: unable to walk, decreased consciousness; 5: death related to ischemia.

C. Elevated Body Swing Test: When measuring, the tail root of the rat is first lifted by hand, the head of the rat is about 5 cm from the plane, at this time, the head of the rat will rotate to the left or right, when the angle of unilateral rotation is greater than 100, the counting standard is recorded, the direction and angle of rotation are recorded, after one test, the rat is allowed to rest for one minute, then the next test was performed again and repeated 20 times, the total direction and number were recorded.

Data Statistics Method

GraphPad Prism 6.0 (GraphPad software, LA Jolla, CA., USA) was used for data analysis, all measurement data are expressed in mean±standard deviation, and one-way ANOVA is used to confirm whether the variance is homogeneous. If the n values are consistent, Tukey method was used for comparison; if the n values are inconsistent, Bonferroni method was used for comparison, and the P<0.05 represent having statistical significance.

2. Animal Experiment

Example 1

1.1 Preparation of Myocardial Infarction Model

Pentobarbital sodium (40 mg/kg) was injected intraperitoneally, the rat was fixed on a operation plate, the chest was shaved and a pen-shaped venous indwelling needle sleeve was inserted into the trachea and connected to a animal ventilator. Disinfection with iodine, the skin was cut on the left side of the chest between 3-4 ribs and the muscle was bluntly detached, the space between the third and fourth ribs was opened and fixed to expose the upper part of the heart, the pericardium was teared apart, a 5-0 strip suture needle was hold by a needle holder, using the left coronary vein as a mark, and thread 1 mm below the junction of the apex of left atrial appendage, the pulmonary conus and the atrial appendage, and the myocardial tissue changed from red to pale immediately after the coronary artery was ligated. Except that the left anterior descending of coronary artery was not ligated, the other surgical procedures in sham-operated animals were exactly the same.

1.2 Group of Animals and Mode of Administration 56 rats were randomly divided into the following 7 groups: sham operation group, ischemia model group, salvianolic acid B and ginsenoside Rg1 combined administration group (prepared according to the ratio of 5:4, 5:3, 5:2, 5:1 and 2:5 respectively), 8 rats per group. The drug is administered in a double-blind way, that is, the operator does not participate in the administration, and the data statisticians do not know the grouping information. Salvianolic acid B and ginsenoside Rg1 were mixed at 5:4, 5:3, 5:2, 5:1, 2:5, respectively, and were randomly numbered after mixing. After dissolving, they were filtered with a microporous filter membrane for later use. The sham operation group and the myocardial infarction model group were given equal volume of normal saline according to body weight. Immediately after the operation, 15 mg/kg was given once via tail vein injection, and the drug was given again 24 hours later. Then blood was taken from abdominal aorta and heart was collected for cardiac histological examination.

1.3 Results and Analysis of Experiments 1.3.1 SalB/Rg1 Reduces Cardiac Infarct Size As shown in FIG. 1, the sham operation group had no infarct area (0%). Compared with the ischemia model group, the infarct size in group 2:5 decreased by 23.4%; the infarct size in group 5:4 decreased by 15.3%; the infarct size in group 5:3 decreased by 35.2% (P<0.01); the infarct size in group 5:2 decreased by 33.2% (P<0.01); the infarct size in group 5:1 decreased by 25.1%; * indicates compared with sham operation group, ***P<0.001; $^{\#}$indicates compared with ischemia model group, $^{\#}$P<0.05. In addition, the 5:3 group and 5:2 group have more obvious effect on reducing the infarct size than the 2:5 group, and the infarct size is 1.50 times (5:3) and 1.42 (5:2) times lower than the 2:5 group, respectively.

1.3.2 SalB/Rg1 Reduces LDH Content in Blood

Figure 2:
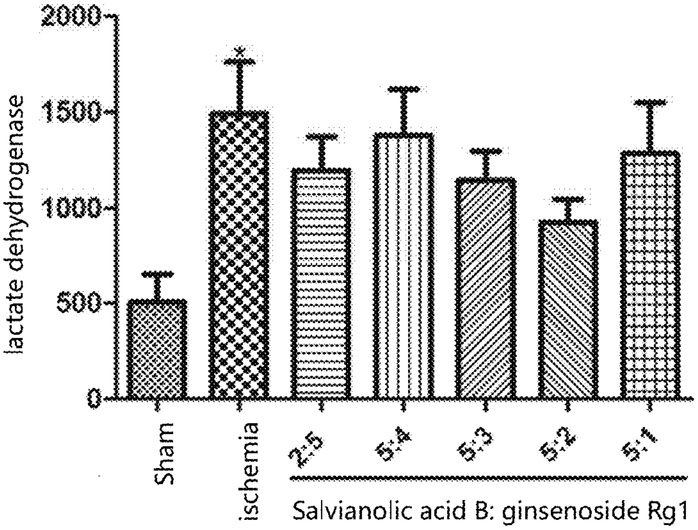
FIG. 2 shows the effect of salvianolic acid B/ginsenoside Rg1 on blood lactate dehydrogenase content in an animal model of myocardial infarction.

Blood LDH content results are shown in FIG. 2. Compared with ischemia model group, LDH content in 2:5 group decreased by 19.7%; LDH content in group 5:4 decreased by 7.5%; LDH content in group 5:3 decreased by 23.0%; LDH content in group 5:2 decreased by 37.9%; LDH content in group 5:1 decreased by 13.7%. * indicates compared with sham operation group, *P<0.05. Compared with 2:5 group, LDH content in 5:2 group decreased 1.9 times.

1.3.3 SalB/Rg1 Improves Cardiac Structure

Figure 3:
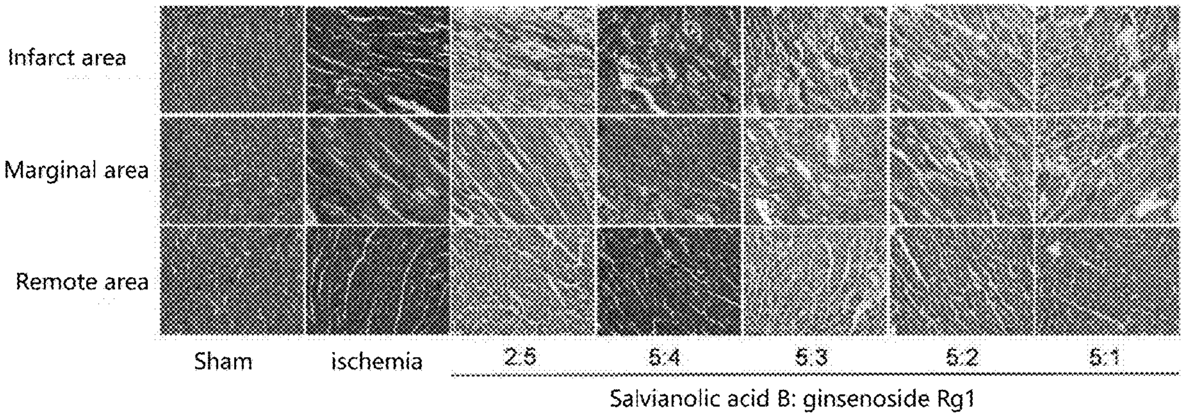
FIG. 3 shows the protective effect of salvianolic acid B/ginsenoside Rg1 on cardiac tissue structure in an animal model of myocardial infarction.

In order to further evaluate the protection of SalB/Rg1 on cardiac tissue structure, the cardiac structure of the infarct area (top), infarct marginal area (middle) and distal infarct area (bottom) of the heart were analyzed respectively (as shown in FIG. 3). In the ischemic model group, the structure of the myocardial infarction area was severely damaged, with infiltration of a large number of inflammatory cells, and the myocardial cells showed edema, necrosis, loss of nucleus, and the muscle fibers were striped; in the marginal area of the infarction, the inflammatory cells obviously infiltrated, and the myocardial fibers became longer and wavy. Compared with the ischemia model group, SalB/Rg1 showed different degrees of improvement on the above injuries in both the infarct area and the infarct marginal area. Among them, the myocardial tissue structure of rats in 5:2 groups was improved most obviously: in the infarct area, inflammatory cell infiltration was significantly reduced, myocardial cell edema and necrosis were weakened, the number of nuclear loss was reduced, and muscle fibers were arranged regularly; in the infarct marginal area, inflammatory cell infiltration was reduced and myocardial fibers were regularly aligned. The cells of each group in the distal infarct region were arranged orderly and tightly and regularly, and there was no significant difference.

The above results show that compared with the ischemia model group, the combined administration of SalB/Rg1 has an effect on reducing the infarct size, and surprisingly, compared with the best ratio of SalB/Rg1 disclosed in the prior art (2:5), after administration the group that SalB/Rg1 is 5:3 and 5:2 in the present invention, the infarct area of the rat heart is smaller, and it shows more excellent therapeutic effect on reducing LDH content in blood and improving cardiac structure.

Example 2

Further Comparison was made in a Myocardial Ischemia-Reperfusion Injury Model using a Combination of SalB/Rg1 of 5:2 in the Prior Art and an Optimal Combination of SalB/Rg1 of 2:5 Disclosed 2.1 Preparation of Myocardial Ischemia Reperfusion Injury Model Pentobarbital sodium (40 mg/kg) was injected intraperitoneally, the rats were fixed on a operation plate, the chest was shaved and a pen-shaped venous indwelling needle sleeve was inserted into the trachea and connected to a animal ventilator. Disinfection with iodine, the skin was cut open on the left side of the chest between 3-4 ribs and the muscle was bluntly detached, the space between the third and fourth ribs was opened and fixed to expose the upper part of the heart, the pericardium was teared apart, a 5-0 suture needle with thread was hold by a needle holder, using the left coronary vein as a mark, and thread 1 mm below the junction of the apex of left atrial appendage, the pulmonary conus and the atrial appendage, a 2-0 thread was placed in the place where the two threads are knotted and ligated, and the myocardial tissue changed from red to pale immediately after the coronary artery was ligated. After 40 minutes of myocardial ischemia, the threads were cut open, and the 2-0 thread was removed for myocardial ischemia reperfusion, and all tests were evaluated after 1 hour. Except that the left anterior descending of coronary artery was not ligated, the other surgical procedures in sham-operated animals were exactly the same.

2.2 Group of Animals and Mode of Administration 16 rats weighing about 220 g were randomly divided into the following two groups: salvianolic acid B and ginsenoside Rg1 combined administration group (which was prepared according to the ratio of 5:2 and 2:5), 8 rats per group. After 40 minutes of myocardial ischemia, the rats were reperfused, at the same time, 15 mg/kg drug were injected via the tail vein immediately. After reperfusion for 1 hour, the hemodynamics detection were preformed, and then the hearts were collected for cardiac histological detection.

2.3 Experimental Results

Figure 4:
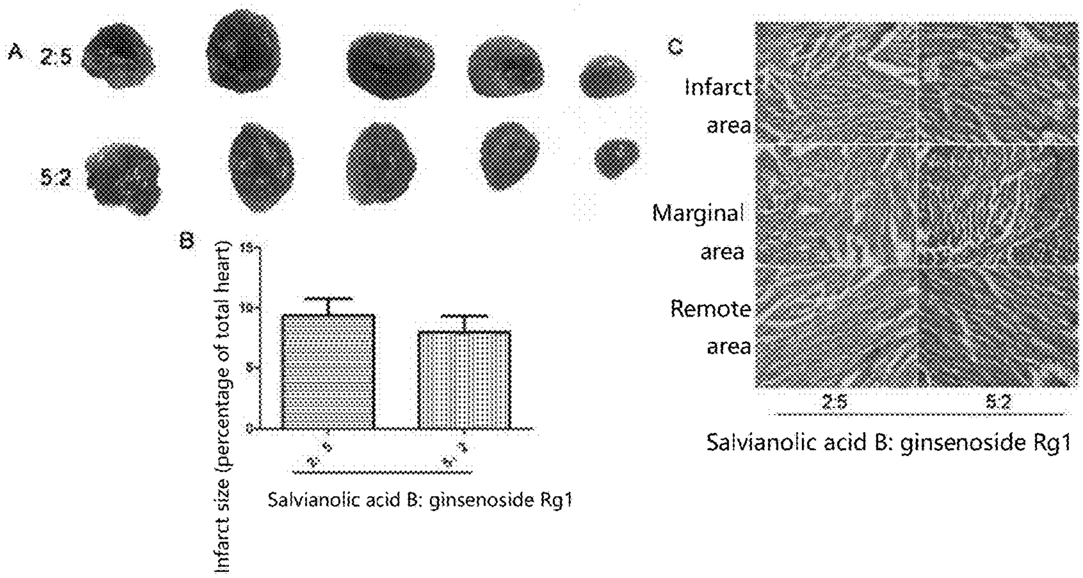
FIG. 4 shows that in the animal model of myocardial ischemia-reperfusion injury, the salvianolic acid B/ginsenoside Rg1 (5:2) group significantly reduced the size of cardiac infarction and improved the cardiac structure than the salvianolic acid B/ginsenoside Rg1 (2:5) group; (A) representative photographs of TTC staining of heart sections; (B) quantification of infarct size (area percentage of infarcted area over the whole heart); (C) representative photographs of HE staining of cardiac tissue.

In the model of cardiac ischemia-reperfusion injury, the experimental results are shown in FIG. 4. Figure A shows representative photographs of the infarct size TTC staining, Figure B shows the quantitative results of infarct size, and Figure C shows representative photographs of the HE staining. Compared with SalB/Rg1 (2:5) group, the infarct size of rat heart of SalB/Rg1 (5:2) group decreased by 15.03%. In order to further evaluate the protection of SalB/Rg1 on cardiac tissue structure after ischemia-reperfusion injury, the cardiac structure of the infarct area (top), infarct marginal area (middle) and distal infarct area (bottom) of the heart were analyzed respectively (Figure C). Compared with SalB/Rg1 (2:5), SalB/Rg1 (5:2) significantly inhibited inflammatory cell infiltration, myocardial cell necrosis, nuclear loss and other damage in the infarct area and the infarct marginal area. The cells of each group in the distal infarct area were arranged orderly and tightly and regularly, and there was no significant difference.

Figure 5:
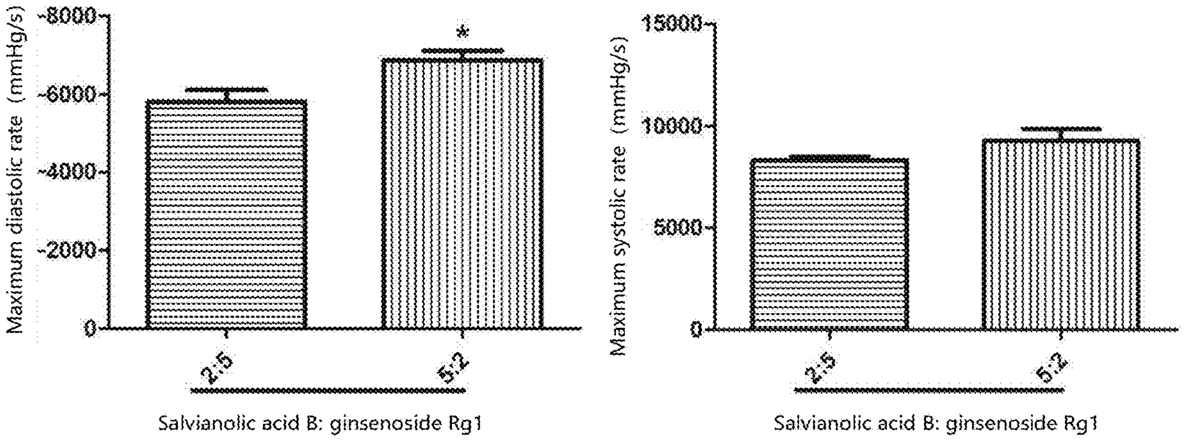
FIG. 5 shows results of hemodynamics (maximum diastolic rate and maximum diastolic rate) of rats in the salvianolic acid B/ginsenoside Rg1 (2:5) group and salvianolic acid B/ginsenoside Rg1 (5:2) group on the animal model of myocardial ischemia-reperfusion injury. "*" means $P<0.05$ compared with salvianolic acid B/ginsenoside Rg1 (2:5) group.
Figure 6:
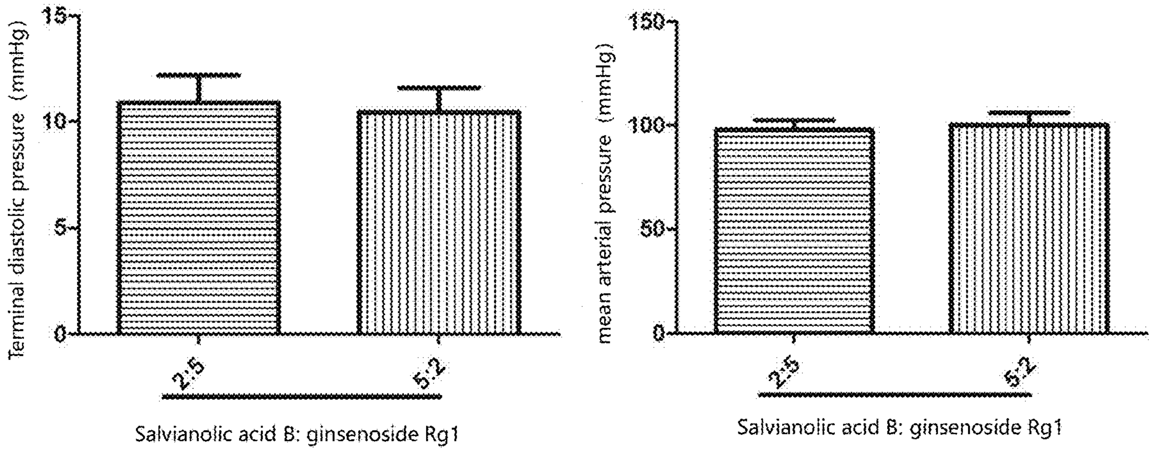
FIG. 6 shows the results of hemodynamics (terminal diastolic pressure and mean arterial pressure) of rats in the salvianolic acid B/ginsenoside Rg1 (2:5) group and salvianolic acid B/ginsenoside Rg1 (5:2) group on animal models of myocardial ischemia-reperfusion injury.

FIGS. 5 and 6 show hemodynamic results, compared with SalB/Rg1 (2:5), SalB/Rg1 (5:2) increases the maximum diastolic rate by 18.2% ($P<0.05$) and increases the maximum systolic rate by 11.6%, indicating that SalB/Rg1 (5:2) have more excellent effects on improving cardiac function than SalB/Rg1 (2:5); FIG. 6 shows that there is no significant difference between terminal diastolic pressure and mean arterial pressure, indicating that SalB/Rg1 (5:2) has no adverse effect on blood pressure regulation compared with SalB/Rg1 (2:5).

Example 3

SalB/Rg1 (5:2) and SalB/Rg1 (2:5) were further compared in renal ischemia reperfusion injury model.

3.1 Preparation of Renal Ischemia Reperfusion Injury Model

Pentobarbital sodium (40 mg/kg) was injected intraperitoneally, the rats were fixed on the operating plate, the abdomen was shaved and disinfected with iodine, and a 2.5 cm incision was made in the middle of the abdomen, the intestinal tract was separated to expose the left kidney, the fat surrounding the kidney was separated, the left renal pedicle (including renal artery, renal vein and renal pelvis) was clamped off via a artery clamp for 40 minutes to cause renal ischemia, and the right kidney were operated the same as the left kidney. After 40 minutes, the artery clamp of the left and right kidneys were removed, kidney ischemia-reperfusion injury were caused 24 hours later, and muscles and skin were sutured. The operation of the sham-operated animals is identical except that the renal pedicles on both sides were not clamped off.

3.2 Group of Animals and Mode of Administration 32 rats were randomly divided into the following 4 groups: sham operation group, ischemia-reperfusion model group, salvianolic acid B and ginsenoside Rg1 combined administration group (which was prepared according to the ratio of 5:2 and 2:5), 8 rats per group. The sham operation group and the renal ischemia-reperfusion model group were given equal volume of normal saline according to body weight. After 40 minutes of renal ischemia, the rats were reperfused again, at the same time, 15 mg/kg drug was injected via tail vein immediately, and the drug was given again 24 hours later. Then the kidneys were collected for renal histological examination.

3.3 Experimental Results

Figure 7:
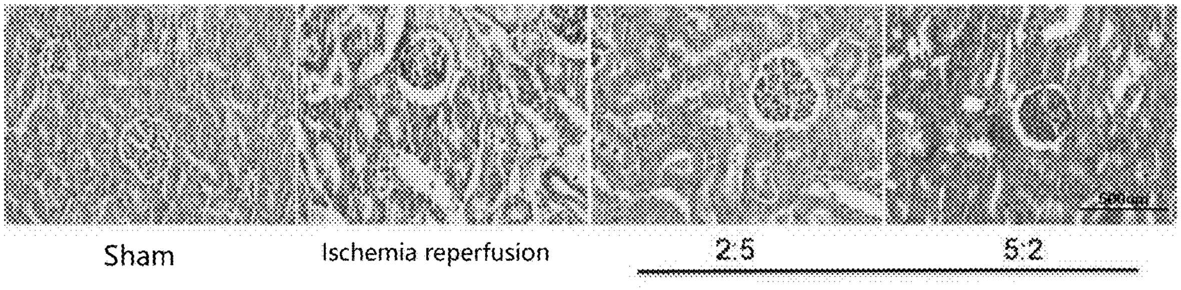
FIG. 7 shows the results of HE staining of rats in the sham operation group, renal ischemia-reperfusion model group, salvianolic acid B/ginsenoside Rg1 (2:5) group and salvianolic acid B/ginsenoside Rg1 (5:2) group on the renal ischemia-reperfusion injury model.

In order to evaluate the protection of SalB/Rg1 on renal tissue structure with ischemia-reperfusion injury, the structure of renal cortex was analyzed (FIG. 7). The renal cortex of ischemia-reperfusion model group had a large number of inflammatory cell infiltration, a large number of erythrocyte exudatio, and increased intercellular space. Compared with the ischemia-reperfusion model group, SalB/Rg1 showed different degrees of improvement on the above injuries, and the renal tissue structure of rats in 5:2 groups was the most obvious improvement: renal cortex inflammatory cell infiltration and erythrocyte exudation were significantly reduced, and the intercellular space was reduced.

Figure 8:
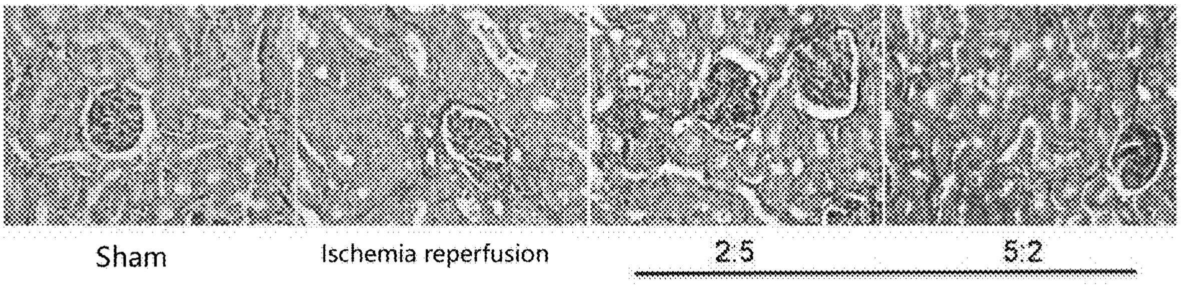
FIG. 8 shows the results of periodic acid-schiff staining (PAS) of rats in the sham operation group, renal ischemia-reperfusion model group, salvianolic acid B/ginsenoside Rg1 (2:5) group and salvianolic acid B/ginsenoside Rg1 (5:2) group on the renal ischemia-reperfusion injury model.

In order to evaluate the effect of SalB/Rg1 on glycogen accumulation in renal tissue with ischemia-reperfusion injury, the glycogen accumulation in renal cortex was analyzed (see FIG. 8). In the ischemia-reperfusion model group, glycogen aggregated in the renal mesangial area, glomerular mesangial cell proliferated, basement membrane thickened, and nucleus exfoliated. Compared with the ischemia-reperfusion model group, SalB/Rg1 showed different degrees of improvement to the above injuries. Compared with the 2:5 group, the renal glycogen accumulation in the 5:2 group was significantly reduced, the proliferation of glomerular mesangial cells was improved, and the number of nucleus exfoliation was reduced.

Example 4

To evaluate the preventive effect of combination of salvianolic acid b/ginsenoside Rg1 (5:2) on pulmonary embolism and its complications in rats 4.1 Experimental Animals and Model Preparation 30 male Wistar rats were randomly divided into the following three groups: normal control group, model control group and salvianolic acid B/Rg1 group (20 mg/kg), 10 rats per group. The normal control group was given normal saline at a dose of 5 ml/kg on day 0, 7, 14 and 21 respectively, and the other two groups were given polystyrene microspheres at the corresponding time. The concentration of polystyrene microspheres is 200,000 particles/ml and the diameter is 45 μm. Wistar rats were injected polystyrene microspheres via tail vein at a dose of 1 millionparticles/kg (5 ml/kg) on day 0, 7, 14 and 21, respectively.

Among two groups of animals given with polystyrene microspheres, one group was injected with normal saline everyday started on the 7th day and used as model control group, and the other group was injected salvianolic acid B/Rg1 (ratio 5:2) intraperitoneally at a dose of 20 mg/kg everyday started on the 7th day for 28 consecutive days. All animals were taken on the 35th day for cardiac and pulmonary histological examination.

Figure 9:
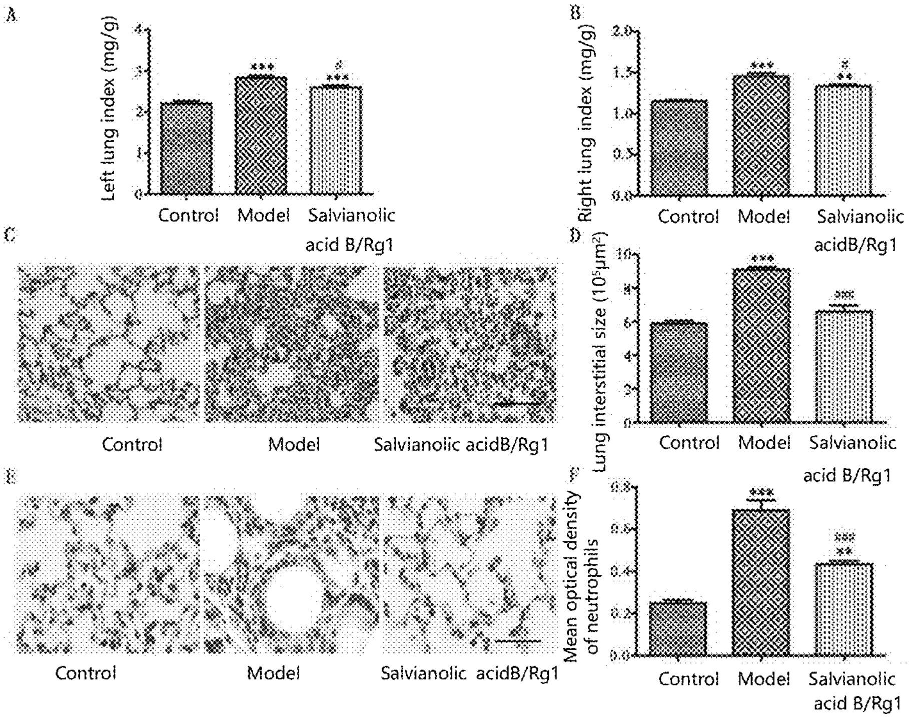
FIG. 9 shows the therapeutic effect of salvianolic acid B/Rg1 (5:2) on pulmonary embolism model; (A) left lung index; (B) right lung index; (c) representative photographs of lung HE staining; (D) quantitative result of lung interstitial size; (E) representative photographs of cardiac HE staining; (F) lung neutrophil average optical density.

4.2 Experimental Results 4.2.1 The Combination of Salvianolic Acid B/Rg1 (5:2) Improves the Pulmonary Embolism Induced by Microspheres The combination of salvianolic acid B/Rg1 can improve the pulmonary embolism induced by microspheres. As shown in FIG. 9, compared with the model group, salvianolic acid B/Rg1 significantly reduced the left lung index (A) and the right lung index (B); it can be seen from the tissue stain that salvianolic acid B/Rg1 significantly improved the lung structure (C) and significantly reduced the area of pulmonary interstitium (D), which proved the effect of salvianolic acid B/Rg1 on improving lung function. In addition, it can be seen from (E) that salvianolic acid B/Rg1 can also inhibit neutrophil infiltration in lung tissue, and its inhibitory effect has significant statistical significance (F), suggesting that salvianolic acid B/Rg1 significantly inhibits the occurrence of pulmonary embolism.

Figure 10:
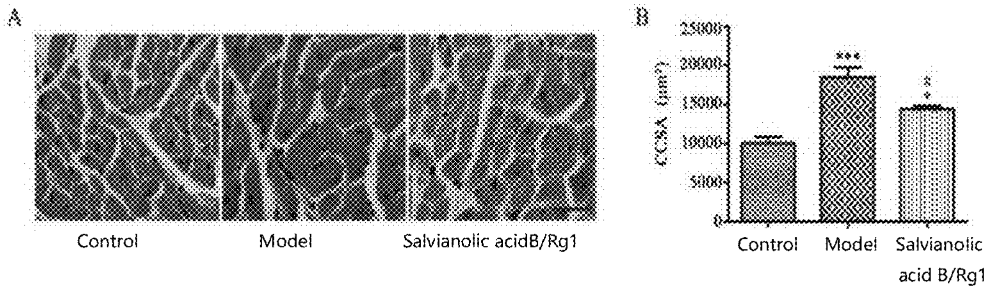
FIG. 10 shows that salvianolic acid B/Rg1 (5:2) reduces the occurrence of myocardial hypertrophy induced by pulmonary embolism on a pulmonary embolism model, (A) representative photographs of cardiac HE staining, (B) a quantitative graph of the cross-sectional area of myocardial cells.

4.2.2 Combination of Salvianolic Acid B/Rg1 Improves Myocardial Hypertrophy Caused by Pulmonary Embolism The main complication of pulmonary embolism is myocardial hypertrophy. On HE-stained myocardial tissue, hypertrophic myocardial cells can be evaluated by the size of cell cross-sectional area. As shown in FIG. 10, A is a representative plot of HE staining of the heart, B is a quantitative plot of the cross-sectional area of myocardial cells, indicating that salvianolic acid B/Rg1 significantly reduces the occurrence of myocardial hypertrophy induced by pulmonary embolism.

Example 5

Combination of Salvianolic acid B/Rg1 (5:2) in the Treatment of Acute Cerebral Infarction in Rats 5.1 Experimental Animals and Model Preparation 30 male SD rats were randomly divided into the following 3 groups: sham operation group, acute cerebral infarction model group, salvianolic acid B/ginsenoside Rg1 combination group (the combination group ratio is 5:2, administration and dose is 10 mg/kg), 10 rats per group. After performing anesthesia, fixation, chest shaving and disinfection with iodine on the rats, the muscle, subcutaneous connective tissue, and anterior cervical muscle group were separated in sequence to expose common carotid artery (CCA); a small opening was cut at 4 mm from CCA bifurcation, the plug line was inserted into the internal carotid artery (ICA) from the small opening, and the plug line was pushed about 20 mm from the blood vessel bifurcation, blocking the middle cerebral artery (MCA) to induce cerebral infarction. Animals with cerebral infarction were treated with 10 mg/kg salvianolic acid B/ginsenoside Rg1 (salvianolic acid B/Rg1 group); animals with cerebral infarction were given normal saline (model group); the animals in the sham operation group were undergo same surgical procedures except inserting the plug line and were given normal saline at the same time point (sham operation group).

Figure 11:
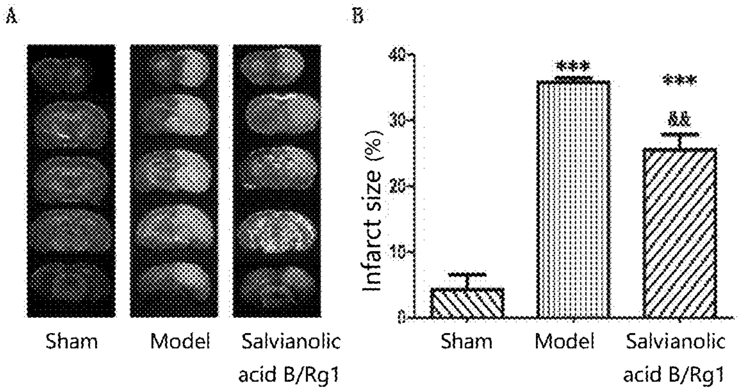
FIG. 11 shows that salvianolic acid B/Rg1 (5:2) significantly reduces the infarct size in the acute cerebral infarction model, (A) representative photographs of brain TTC staining, (B) quantitative results of infarct size.

5.2 Experimental Results 5.2.1 Salvianolic Acid B/Rg1 Reduces Cerebral Infarction Size The cerebral infarction size was evaluated by TTC staining, as shown in FIG. 11, wherein Figure A shows representative photographs of brain TTC staining, with the infarcted area being stained white and the non-infarcted area being stained red. Fig. B shows the quantitative result of infarct size (percentage of white area size/(red area size+white area size)), salvianolic acid B/Rg1 significantly reduced the infarct size, compared with the model group, the infarct size in salvianolic acid B/Rg1 group decreased by 39.42%. Note: ***$p<0.001$ VS sham operation group, & & $p<0.01$ VS model group.

Figure 12:
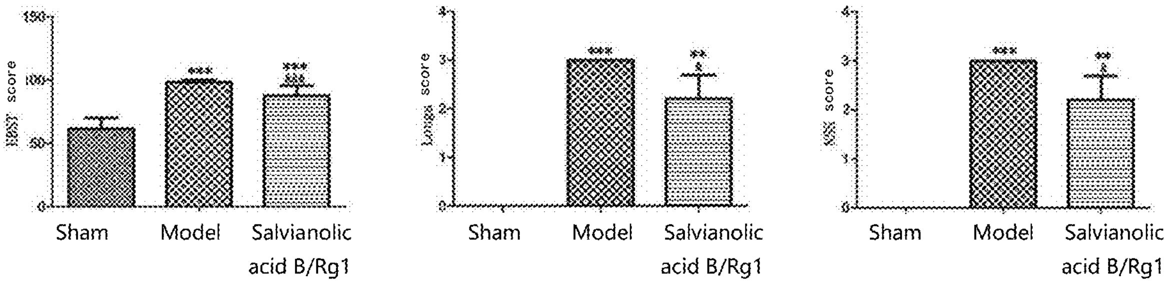
FIG. 12 shows that salvianolic acid B/Rg1 (5:2) improved the results of behavioral score of rats after cerebral infarction on the acute cerebral infarction model.

5.2.2 Salvianolic Acid B/Rg1 Improves Behavior Score of Rats after Cerebral Infarction Longa score, NSS score and EBST were used to evaluate the neuromotor function of rats before and after the operation. The results are shown in FIG. 12. According to the three scoring methods, there was no obvious behavioral difference among the three groups of animals before surgery. After cerebral infarction modeling, salvianolic acid B/Rg1 significantly improved neuromotor function according to EBST score ($p<0.001$), Longa score ($p<0.05$) and NSS score ($p<0.05$).

5.2.3 Salvianolic acid B/Rg1 Protects Cerebral Cortical Nerve Cells

Figure 13:
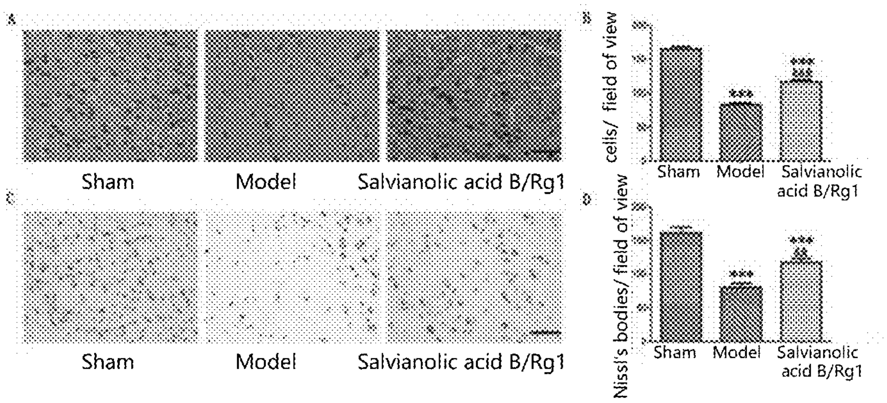
FIG. 13 shows the protective effect of salvianolic acid B/Rg1 (5:2) on cerebral cortical nerve cells in an acute cerebral infarction model, and (A) is the HE staining representative photographs of the cerebral cortex; (B) is the quantitative result of the number of nerve cells stained by HE; (C) is the representative photographs of the cerebral cortex with Nissl's staining; (D) is the quantitative result of the number of Nissl bodies in cerebral cortex.

The cerebral cortex is a high-level center that regulates and controls body movement. As shown in FIG. 13, A is the HE staining representative photographs of the cerebral cortex; B is the quantitative result of the number of nerve cells in the field of view of a single image of HE staining; C is the Nissl's staining representative photographs of the cerebral cortex; D is the quantitative result of the number of Nissl bodies in the cerebral cortex in the field of view of a single image. The results showed that salvianolic acid B/Rg1 has significant protective effect on nerve cells in both HE staining and Nissl's staining. Note: ***$p<0.001$ VS sham operation group, & & $p<0.01$, & & & $p<0.001$ VS model group.

5.2.4 Salvianolic Acid B/Rg1 Protects Hippocampal Neurons

Figure 14:
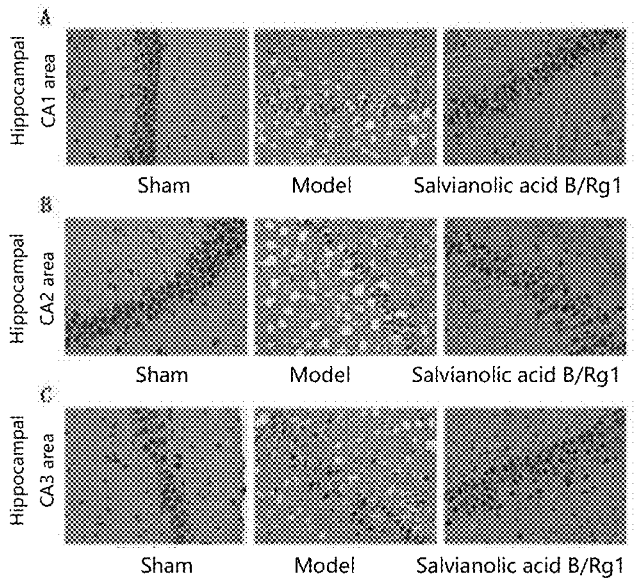
FIG. 14 shows the representative photographs of HE staining of the hippocampus CA1, CA2, and CA3 in the acute cerebral infarction model.

From an anatomical point of view, the hippocampus is often regarded as a medial protrusion of the frontal eminence of the lateral ventricle, which consists of four regions: CA1, CA2, CA3 and CA4. The cytoplast of nerve cells are arranged in layers with their neural network areas. FIG. 14 is a HE staining diagram of CA1, CA2, and CA3. Compared with the sham operation group, the model group showed obvious vacuolization, neuronal cell body shrinkage, loss and reduced in number; compared with the model group, the salvianolic acid B/Rg1 group has increased surviving neuronal cells, well-arranged neuronal cells and significantly elevated number of neuronal cells.

Figure 15:
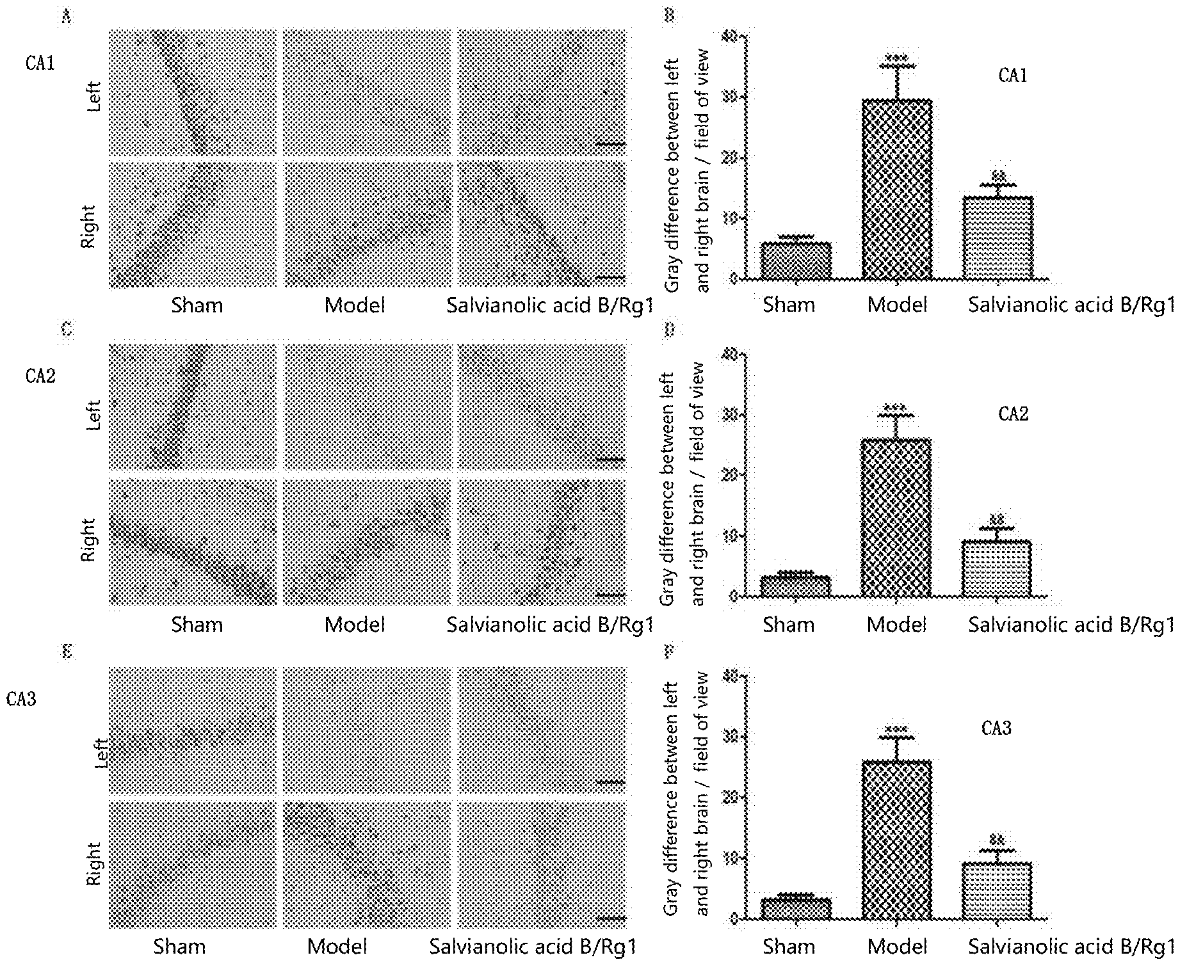
FIG. 15 shows the representative photographs of the Nissl's staining of the hippocampus CA1, CA2, and CA3 and their quantitative results in the acute cerebral infarction model.

FIG. 15 is a representative photographs diagram of the Nissl's staining of CA1, CA2, and CA3 and their quantitative results. The number of cells shown in the representative photographs (A, B, C) of Nissl's staining in CA1, CA2 and CA3 regions is consistent with the trend of HE staining. The left brain of this animal model is the site of injury, and the right brain presents normal histological structure. The gray difference/image field of left and right brain reflects the damage degree of nerve cells in model animals, the quantitative results of Figures B, D and F show that salvianolic acid B/Rg1 protects the integrity of nerve cells. It can be seen from FIG. 15-16 that salvianolic acid B/Rg1 shows protective effects on hippocampal CA1, CA2 and CA3 in both HE staining and Nissl's staining.

Example 6

Combination of Salvianolic acid B/Rg1 (5:2) in the treatment of cerebral ischemia-reperfusion injury in rats 6.1 Experimental Animals and Model Preparation 30 male SD rats were randomly divided into the following 3 groups: sham operation group, cerebral ischemia-reperfusion injury model group, edaravone (purchased from Sinopharm Group Guorui Pharmaceutical Co., Ltd., batch number: 1909116) group, butylphthalide (purchased from Enbipu Pharmaceutical Co., Ltd., batch number: 6182002117) group, salvianolic acid B/Rg1 combined group (5:2, administration dose 5 mg/kg), 10 rats per group.

After performing anesthesia, fixation, chest shaving and disinfection with iodine, the muscle, subcutaneous connective tissue, and anterior cervical muscle group were separated in sequence to expose common carotid artery (CCA) of rats; a small opening was cut at 4 mm from CCA bifurcation, the plug line was inserted into the internal carotid artery (ICA) from the small opening, and the plug line was pushed about 20 mm from the blood vessel bifurcation, blocking the middle cerebral artery (MCA) for 2 h to induce cerebral infarction, and then the plug line was pulled out to prepare a model of cerebral ischemia for 2 h and reperfusion for 24 h. Administration (tail vein injection) were performed 10 minutes before pulling out the plug line: administering 5 mg/kg salvianolic acid B/ginsenoside Rg1 (salvianolic acid B/Rg1 group); administering 5 mg/kg edaravone (edaravone group, based on effective ingredients); 5 mg/kg butylphthalide (butylphthalide group, based on effective ingredients); administering 5 mg/kg normal saline (model group); all surgical procedures were identical in sham operation group, except that no plug line was inserted, and 5 mg/kg normal saline was given.

Figure 16:
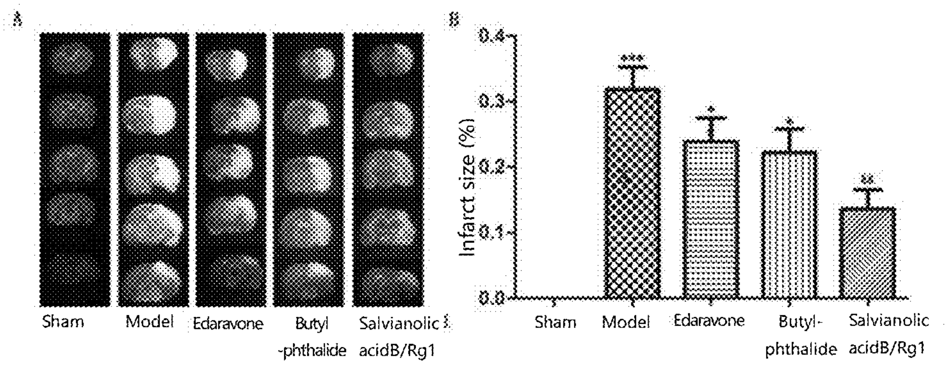
FIG. 16 shows that salvianolic acid B/Rg1 (5:2) reduces the infarct size of reperfusion injury in a cerebral ischemia-reperfusion injury model, (A) representative photographs of TTC staining of brain tissue, and (B) quantitative results of infarct size.

6.2 Experimental Results 6.2.1 Salvianolic Acid B/Rg1 Reduces Cerebral Infarction Size of Reperfusion Injury As shown in FIG. 16, the size of cerebral infarction is evaluated by TTC staining. The representative photographs of the staining results of each group is shown in Figure A, and the quantitative result of infarct size is shown in Figure B. It can be seen that compared with edaravone and butylphthalide, salvianolic acid B/Rg1 has a more significant effect on reducing infarct size. Note: ***$p<0.001$, *$p<0.1$VS sham operation group, & & $p<0.01$ VS model group.

Figure 17:
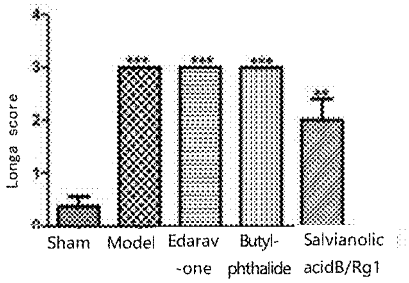
FIG. 17 shows that salvianolic acid B/Rg1 (5:2) improves the behavioral score of rats after cerebral ischemia-reperfusion on cerebral ischemia-reperfusion injury model.

6.2.2 Salvianolic Acid B/Rg1 Improves Behavior Score of Rats after Cerebral Ischemia Reperfusion Longa score was used to evaluate the neuromotor function of rats before and after operation. The results are shown in FIG. 17. According to Longa scoring method, there was no obvious behavioral difference among the five groups of animals before surgery. After modeling, according to Longa evaluation, salvianolic acid B/Rg1 showed better effect on improving neuromotor function than edaravone and butylphthalide.

6.2.3 Salvianolic Acid B/Rg1 Protects Cerebral Cortical Nerve Cells

Figure 18:
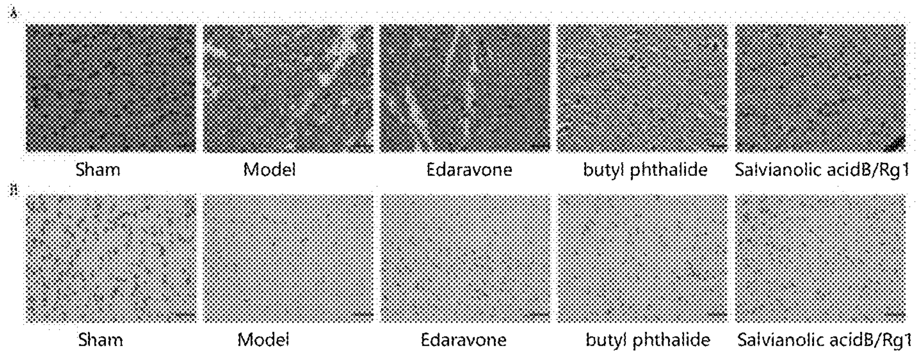
FIG. 18 shows the protective effect of salvianolic acid B/Rg1 on cerebral cortex nerve cells in a cerebral ischemia-reperfusion injury model, A is HE staining of cerebral cortex; B is Nissl's staining of cerebral cortex.

As shown in FIG. 18, A shows HE staining of cerebral cortex; B shows Nissl's staining of cerebral cortex. Compared with the sham operation group, the model group showed obvious vacuolization, neuronal cell body shrinkage, loss, and reduced in number. Compared with the model group, the survival of nerve cells in salvianolic acid B/Rg1 group was significantly higher than that in the model group, edaravone group and butylphthalide group. Whether HE staining or Nissl's staining, salvianolic acid B/Rg1 showed the protective effect on nerve cells, and showed more excellent therapeutic effect than edaravone and butylphthalide.

6.2.4 Salvianolic Acid B/Rg1 Protects Hippocampal Neurons

Figure 19:
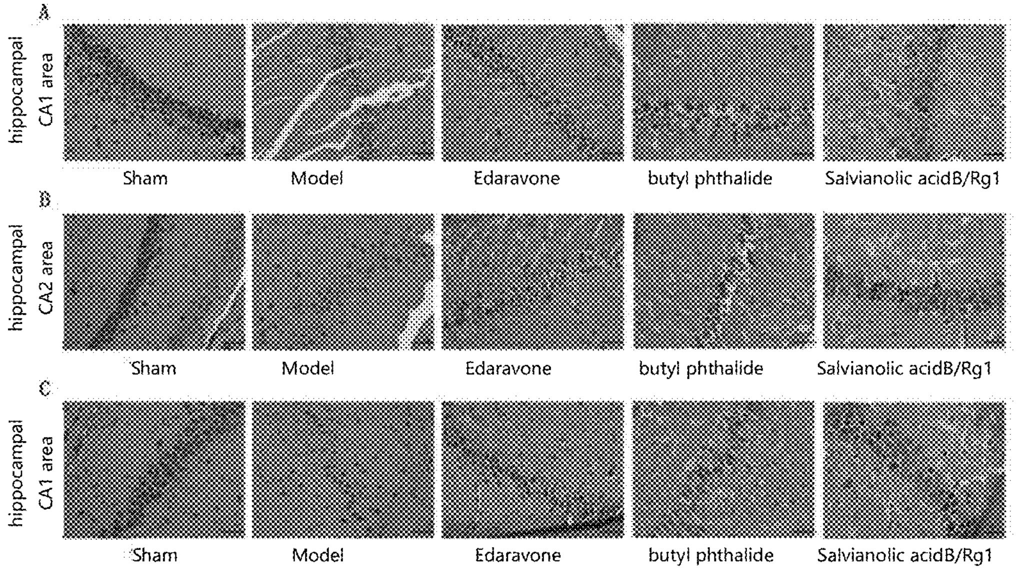
FIG. 19 shows the representative photographs of HE staining of hippocampus CA1, CA2, and CA3 on the rat cerebral ischemia-reperfusion injury model.
Figure 20:
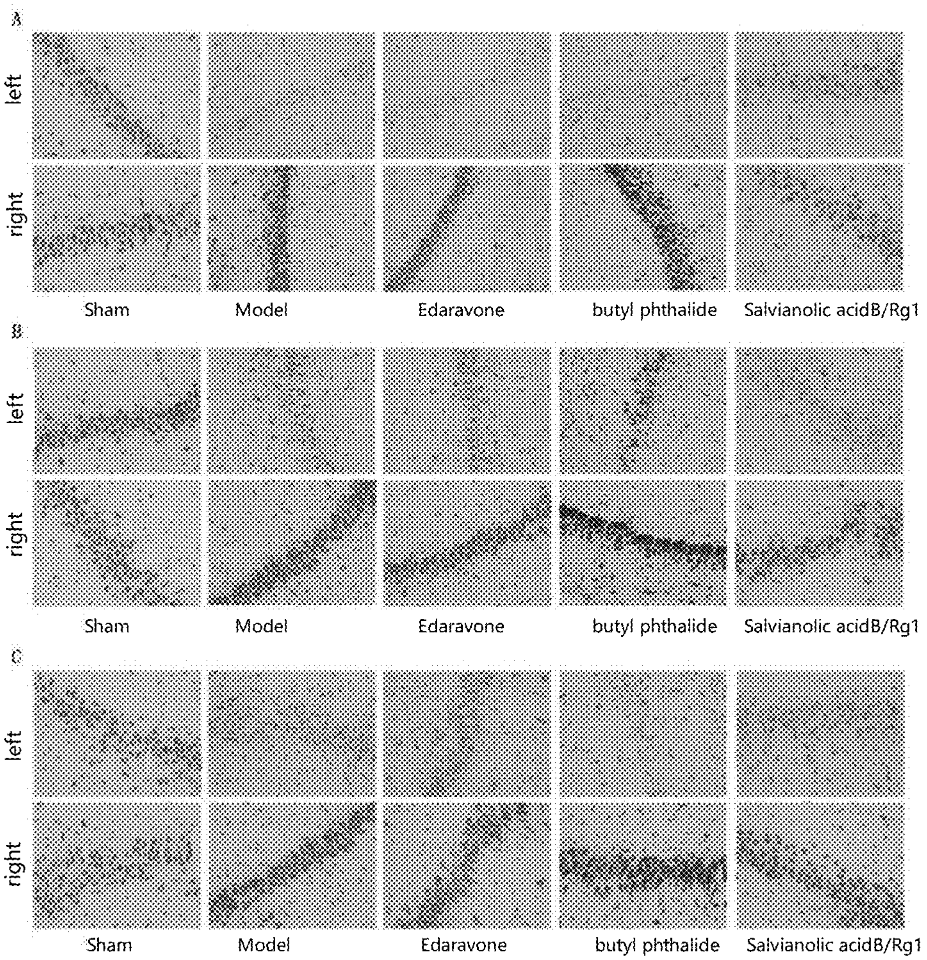
FIG. 20 shows representative photographs of the Nissl's staining of hippocampus CA1, CA2, and CA3 on a rat cerebral ischemia-reperfusion injury model.

FIG. 19 is the HE staining representative photographs of CA1, CA2, and CA3, and FIG. 20 is the representative photographs of CA1, CA2, and CA3. Whether HE staining or Nissl's staining, salvianolic acid B/Rg1 showed the protective effect on hippocampal CA1, CA2 and CA3, and showed more excellent therapeutic effect than edaravone and butylphthalide.

Example 7

Protective effect of salvianolic acid b/ginsenoside Rg1 (5:2) on hepatic ischemia-reperfusion injury in rats 7.1 Experimental Animals and Model Preparation 16 male SD rats were randomly divided into two groups, one group was hepatic ischemia-reperfusion injury model group, and the other group was salvianolic acid B/Rg1 (5:2) combination treatment group.

The method for preparing model of liver ischemia-reperfusion injury is as follows; the rats are weighed and anesthetized, the abdomen was sheved, and fixed on the operating table; disinfected with iodine, and the middle of the abdomen was longitudinally incised 5 cm to the xiphoid; the skin, muscles and the peritoneum were cut open to fully expose the liver and gastrointestinal tract; the perihepatic ligaments were separated; the middle lobe of the liver was clamped off via a microhemostatic clip; the left lobe portal vein, hepatic artery and bile duct were exposed; then the color of the liver lobe gradually changed from red to pale, indicating successful in blocking hepatic blood flow. After blocking blood flow for 1 h, the hemostatic clip was removed. The color of liver lobe was gradually ruddy, indicating successful in liver reperfusion. The model control group was given normal saline at the same time of reperfusion; Salvianolic acid B/Rg1 combined group was given 10 mg/kg salvianolic acid B/ginsenoside Rg1 (5:2) at the same time of reperfusion. After 6 hours of reperfusion, the liver protection effect was evaluated.

7.2 Experimental Results

Figure 21:
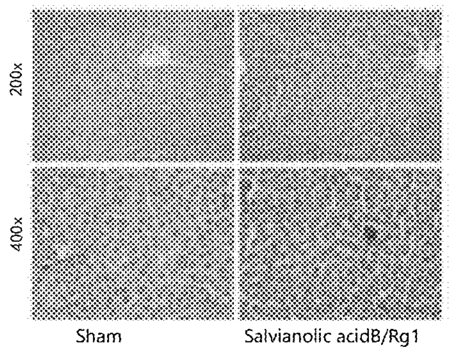
FIG. 21 shows representative photographs of HE staining of liver tissue on a rat hepatic ischemia-reperfusion injury model.

HE staining was performed on the above liver tissues. Results as shown in FIG. 21 (200× in top and 400× in bottom), after 6 hours of ischemia reperfusion, the liver lobular structure in the model group was incomplete, the liver cells were disordered, congested, swollen, and cell necrosis was obvious, while salvianolic acid B/Rg1 could improve the liver cell structure, but the effect was not as obvious as heart and brain.

Discussion

In the prior art, the experimental results show that the effect of different drugs on reducing the infarct size: salvianolic acid B <ginsenoside Rg1<<salvianolic acid B: ginsenoside Rg1=2:5 group, (see CN2011102229806, FIG. 3), so it is easy to think that ginsenoside Rg1 has a better effect on reducing the infarct size of the heart than salvianolic acid B, when being used in combination, the larger proportion of ginsenoside Rg1, the better effect, surprisingly compared with the best ratio of combination (SalB/Rg1 is 2:5) disclosed in the prior art, the pharmaceutical composition of the present invention (salvianolic acid B>ginsenoside Rg1 in weight) shows a more excellent in the trems of treatment of myocardial infarction, cerebral infarction, pulmonary embolism and other ischemic diseases, and cardiac, cerebral ischemia-reperfusion injury (such as reduced infarct size, improved structure and function of tissue and organ). Unexpectedly, the pharmaceutical composition of the present invention can also reduce the concentration of LDH in the blood and/or inhibit the activity of LDH, and can be used as a LDH inhibitor.

Different tissues and organs (such as heart, liver, spleen, lung, kidney, brain, muscle, nerve, etc.), due to their differences in tissue structure, function, blood vessel distribution, and blood demand, etc., whether the drugs have a therapeutic effect on ischemic perfusion injury of different organs or not, the result is difficult to predict. Surprisingly, the pharmaceutical composition of the present invention shows excellent effect of improving organ function not only on the heart, but also on the brain, kidney, liver and other organs with ischemia-reperfusion injury, and can be widely used in a variety of tissues and organs of ischemia-reperfusion injury.

More unexpectedly, the combination of SalB/Rg1 has a better therapeutic effect on ischemic diseases and ischemia-reperfusion injury of heart and brain than that of other tissues and organs, especially the protective effects on cerebral ischemic stroke and reperfusion injury after cerebral ischemic stroke are particularly surprising, not only significantly reduces the infarct size, but also significantly improves the behavior of animals, indicating that the pharmaceutical composition of the present invention has excellent therapeutic prospects for heart diseases and brain diseases.

All documents referred to in the present invention are incorporated by reference herein as if each document is individually incorporated by reference. Further, it should be understood that upon reading the above teaching of the present invention, various modifications or modifications may be made to the present invention by those skilled in the art, and those equivalents also fall within the scope defined by the appended claims of the present application.

The invention claimed is:

1. A pharmaceutical composition, consisting of:

(a) a first active ingredient selected from the group consisting of salvianolic acid B, a stereoisomer thereof, a crystal form thereof, a pharmaceutically acceptable salt, or any combinations thereof;

(b) a second active ingredient selected from the group consisting of ginsenoside Rg1, a stereoisomer thereof, a crystal form thereof, a pharmaceutically acceptable salt, or any combinations thereof; and (c) pharmaceutically acceptable carriers;

wherein, a weight ratio of the first active ingredient to the second active ingredient is 5: (1.9-3.1), wherein the weight ratio is based on the salvianolic acid B and the ginsenoside Rg1.

2. The pharmaceutical composition of claim 1, wherein the weight ratio of the first active ingredient to the second active ingredient is 5:(2-3).

3. The pharmaceutical composition according to claim 1, wherein the first active ingredient is the salvianolic acid B and the second active ingredient is the ginsenoside Rg1.

4. The pharmaceutical composition of claim 1, wherein a dosage form of the pharmaceutical composition is selected from the group consisting of liquid preparations, solid preparations, gaseous forms, and semi-solid forms.

5. The pharmaceutical composition of claim 4, wherein the dosage form is selected from the group consisting of: injections, oral preparations, sublingual preparations, preparations for respiratory administration, preparations for dermal administration, and preparations for mucosal administration.

6. A combination of active ingredients, wherein the combination of active ingredients consists of:

(a) a first active ingredient selected from the group consisting of salvianolic acid B, a stereoisomer thereof, a crystal form thereof, a pharmaceutically acceptable salt, or any combinations thereof;

(b) a second active ingredient selected from the group consisting of ginsenoside Rg1, a stereoisomer thereof, a crystal form thereof, a pharmaceutically acceptable salt, or any combinations thereof;

wherein, a weight ratio of the first active ingredient to the second active ingredient is 5:(1.9-3.1), wherein the weight ratio is based on the salvianolic acid B and the ginsenoside Rg1.

7. A kit, wherein the kit consists of:

a first pharmaceutical composition, consisting of: (a) a first active ingredient selected from the group consisting of salvianolic acid B, a stereoisomer thereof, a crystalline form thereof, a pharmaceutically acceptable salt, or a combination thereof, and a pharmaceutically acceptable carrier; and a second pharmaceutical composition, consisting of: (b) a second active ingredient selected from the group consisting of ginsenoside Rg1, a stereoisomer thereof, a crystal form thereof, a pharmaceutically acceptable salt, or any combinations thereof; and a pharmaceutically acceptable carrier;

wherein, the first pharmaceutical composition and the second pharmaceutical composition are administered in combination and a weight ratio of the first active ingredient to the second active ingredient is 5:(1.9-3.1), wherein the weight ratio is based on the salvianolic acid B and the ginsenoside Rg1.

8. A method for (i) preventing and/or treating of ischemic diseases; and/or (ii) preventing and/or treating of ischemia-reperfusion injury comprising:

administering to a subject in need thereof the pharmaceutical composition according to claim 1.

9. The method of claim 8, wherein the ischemic disease is tissue or organ ischemic injury due to primary lesions of tissues and blood vessels, or at least one ischemic lesions due to secondary causes selected from the group consisting of trauma-induced vascular disconnection, inflammation-induced vascular occlusion, and tumor-induced vascular compression.

10. The method of claim 9, wherein the ischemic disease is selected from the group consisting of ischemic heart disease, ischemic stroke, pulmonary embolism, ischemic liver injury, ischemic nephropathy, ischemic nerve injury, and combinations thereof.

11. The method of claim 10, wherein the ischemic heart disease comprises coronary heart disease, myocardial infarction, angina, myocardial fibrosis, heart failure, or any combinations thereof.

12. The method of claim 8, wherein the ischemia-reperfusion injury is a tissue or organ injury caused by reperfusion.

13. The method of claim 12, wherein the tissue or organ is selected from the group consisting of heart, brain, liver, spleen, lung, kidney, muscle, nerve, and combinations thereof.

14. The method of claim 13, wherein the tissue or organ injury is at least one injury selected from the group consisting of a reperfusion injury after a surgery and a thrombolytic therapy.

15. The method of claim 14, wherein the surgery is selected from the group consisting of: arterial bypass grafting, thrombectomy, percutaneous transluminal coronary angioplasty, cardiac surgery under cardiopulmonary bypass, at least one resuscitation selected from the group consisting of cardiac, pulmonary, and cerebral resuscitation after cardiac arrest, replantation of severed limbs, and organ transplantation.

16. The pharmaceutical composition of claim 1, wherein the weight ratio of the first active ingredient to the second active ingredient is 5:2.

17. The pharmaceutical composition of claim 4, wherein the dosage form of the pharmaceutical composition is selected from the group consisting of injection liquid, powder injections, capsules, tablets, pills, powders, granules, syrups, oral solutions, and tinctures.

18. The pharmaceutical composition of claim 5, wherein the dosage form is injections.

19. The method of claim 9, wherein the weight ratio of the first active ingredient to the second active ingredient is 5:2.

* * * * *